United States Patent
Pevsner et al.

(10) Patent No.: US 7,714,276 B2
(45) Date of Patent: May 11, 2010

(54) METHODS FOR DIRECT BIOMOLECULE IDENTIFICATION BY MATRIX-ASSISTED LASER DESORPTION IONIZATION (MALDI) MASS SPECTROMETRY

(75) Inventors: Paul Pevsner, New York, NY (US); Frederick Naftolin, Woodbridge, CT (US); Douglas C. Miller, Delle Mead, NJ (US); Dean Hillman, New Hyde Park, NY (US); Brian K. Stall, Bedford, NH (US); Steven M. Wishnie, Columbia, MD (US)

(73) Assignee: New York University, New York, NY (US)

( * ) Notice: Subject to any disclaimer, the term of this patent is extended or adjusted under 35 U.S.C. 154(b) by 786 days.

(21) Appl. No.: 11/541,380

(22) Filed: Sep. 29, 2006

(65) Prior Publication Data

US 2007/0114375 A1     May 24, 2007

Related U.S. Application Data

(60) Provisional application No. 60/722,206, filed on Sep. 30, 2005, provisional application No. 60/784,016, filed on Mar. 20, 2006.

(51) Int. Cl.
*B01D 59/44*    (2006.01)
(52) U.S. Cl. ........................................ 250/282; 250/287
(58) Field of Classification Search ................. 250/282; 425/7.23
See application file for complete search history.

(56) References Cited

U.S. PATENT DOCUMENTS

| 6,756,586 B2* | 6/2004 | Caprioli | 250/282 |
|---|---|---|---|
| 2003/0073145 A1* | 4/2003 | Caprioli | 435/7.23 |
| 2005/0029444 A1* | 2/2005 | Caprioli | 250/282 |
| 2006/0219558 A1* | 10/2006 | Hafeman et al. | 204/456 |
| 2007/0031900 A1* | 2/2007 | Caprioli | 435/7.23 |
| 2008/0179512 A1* | 7/2008 | Komatsu et al. | 250/282 |
| 2008/0278706 A1* | 11/2008 | Murayama et al. | 356/36 |

\* cited by examiner

*Primary Examiner*—Nikita Wells
*Assistant Examiner*—Johnnie L Smith
(74) *Attorney, Agent, or Firm*—Klauber & Jackson, LLC

(57) ABSTRACT

The present invention relates to the use of post source decay (PSD) or collision induced dissociation (CID) direct tissue (DT) MALDI-TOF or DT-MALDI-TOF-TOF mass spectrographic identification of biological molecules in a tissue or cellular sample without the need for further protein extraction. This method provides for studying cells or tissues by direct tissue MALDI (DT-MALDI), thereby substituting in situ protein release for further protein extraction. Mass/intensity data was processed with Mascot© software interrogation of the NCBI database. These results are proof of principle that DT-MALDI, combined with bioinformatics, can directly identify proteins in cells and tissues from their mass spectra.

32 Claims, 19 Drawing Sheets

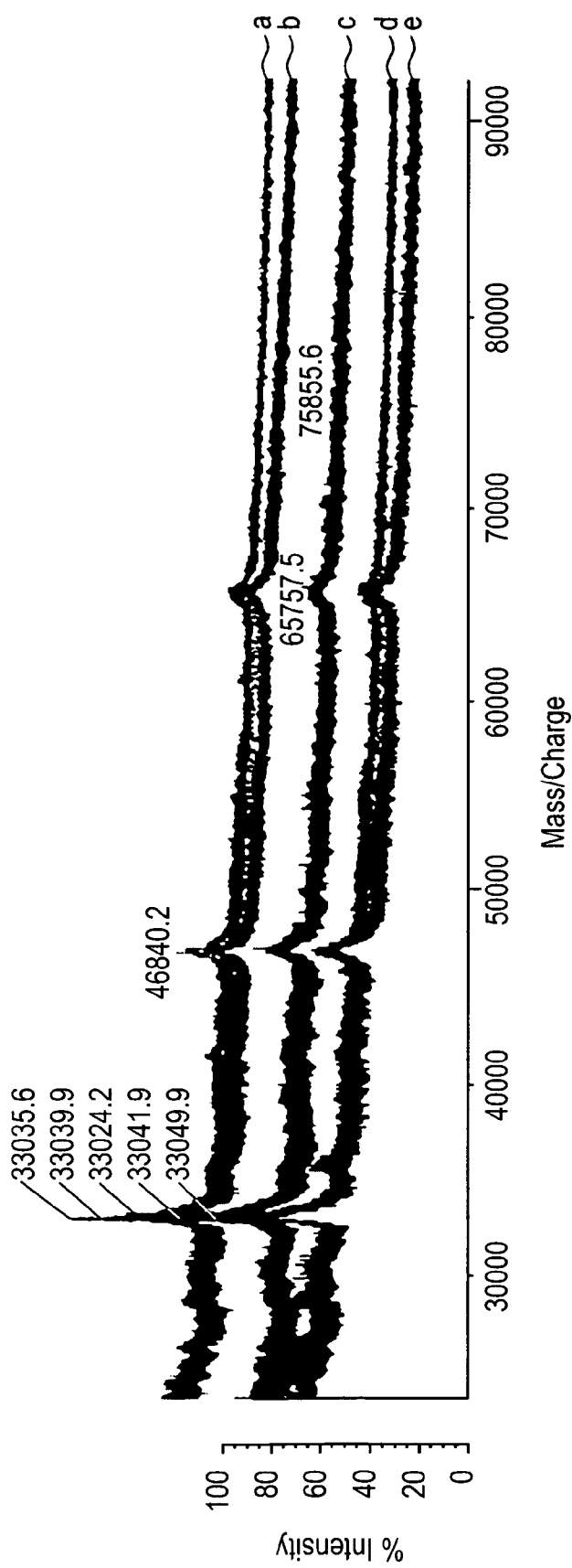

FIGURE 5

Mascot Search Results

```
User          : PHP
Email         : ppvsner1@earthlink.net
Search title  : PSD 1742.8
MS data file  : PSD1742.8 20060207.txt
Database      : NCBInr 20060203 (3284262 sequences; 1125694017 residues)
Taxonomy      : Homo sapiens (human) (140595 sequences)
Timestamp     : 7 Feb 2006 at 18:32:47 GMT
Significant hits: gi|31977  histone H2B [Homo sapiens]
```

Probability Based Mowse Score

Ions score is $-10*\text{Log}(P)$, where P is the probability that the observed match is a random event. Individual ions scores > 38 indicate identity or extensive homology ($p<0.05$).
Protein scores are derived from ions scores as a non-probabilistic basis for ranking protein hits.

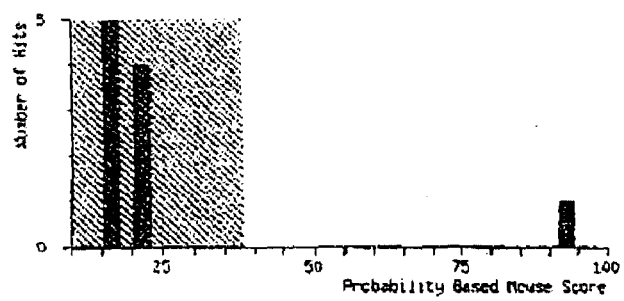

Peptide Summary Report

[Format As]  Peptide Summary                                   Help

Significance threshold p< 0.05        Max. number of hits 20

FIGURE 6

Standard scoring ◉ MudPIT scoring ○ Ions score cut-off 0     Show sub-sets ☐
Show pop-ups ◉ Suppress pop-ups ○ Sort unassigned Decreasing Score    ▨ Require bold red ☐

[Select All] [Select None] [Search Selected]  ☐ Error tolerant 1.  gi|131977       Mass: 13942    Score: 93    Queries matched: 1
    histone H2B (Homo sapiens)
    ☐ Check to include this hit in error tolerant search Query  Observed   Mr(expt)   Mr(calc)   Delta  Miss  Score  Expect  Rank  Peptide
    ☑  1   1742.8000  1741.7927  1742.8119  -1.0192  0    93    2e-07    1   K.AMGIMNSFVNDIFER.I Proteins matching the same set of peptides:
    gi|131979         Mass: 13898    Score: 93    Queries matched: 1
    histone H2A.2 (Homo sapiens)
    gi|32113          Mass: 13506    Score: 93    Queries matched: 1
    unnamed protein product (Homo sapiens)
    gi|184096         Mass: 11324    Score: 93    Queries matched: 1
    histone H2B.1
    gi|1568551        Mass: 13928    Score: 93    Queries matched: 1
    histone H2B (Homo sapiens)
    gi|1568557        Mass: 13928    Score: 93    Queries matched: 1
    histone H2B (Homo sapiens)
    gi|3219590        Mass: 13944    Score: 93    Queries matched: 1
    histone 1, H2b1 (Homo sapiens)
    gi|4995026        Mass: 13880    Score: 93    Queries matched: 1
    histone 1, H2bh (Homo sapiens)
    gi|7264003        Mass: 13981    Score: 93    Queries matched: 1
    histone 1, H2bm (Homo sapiens)
    gi|11036646       Mass: 13936    Score: 93    Queries matched: 1
    H2B histone family, member S (Homo sapiens)
    gi|15680009       Mass: 8644     Score: 93    Queries matched: 1

FIGURE 7

```
HIST1H2BJ protein [Homo sapiens]
gi|45767717      Mass: 14090    Score: 93    Queries matched: 1
H2B histone family, member E [Homo sapiens]
gi|55625974      Mass: 13928    Score: 93    Queries matched: 1
PREDICTED: similar to Histone H2B 291B [Pan troglodytes]
gi|55626043      Mass: 13898    Score: 93    Queries matched: 1
PREDICTED: similar to histone H2b-616 [Pan troglodytes]
gi|55626070      Mass: 13896    Score: 93    Queries matched: 1
PREDICTED: similar to H2B histone family, member R [Pan troglodytes]
gi|55626086      Mass: 13914    Score: 93    Queries matched: 1
PREDICTED: similar to histone H2B [Pan troglodytes]
gi|55626088      Mass: 13898    Score: 93    Queries matched: 1
PREDICTED: similar to H2B histone family, member F [Pan troglodytes]
gi|55930917      Mass: 13882    Score: 93    Queries matched: 1
H2B histone family, member T [Homo sapiens]
gi|55960983      Mass: 13932    Score: 93    Queries matched: 1
histone 2, H2bf [Homo sapiens]
gi|68512407      Mass: 13928    Score: 93    Queries matched: 1
HIST1H2BN protein [Homo sapiens]
gi|73487310      Mass: 14727    Score: 93    Queries matched: 1
Unknown (protein for IMAGE:40002416) [Homo sapiens]
gi|76827222      Mass: 13912    Score: 93    Queries matched: 1
H2B histone family, member Q [Homo sapiens]
gi|78070456      Mass: 13767    Score: 93    Queries matched: 1
HIST1H2BG protein [Homo sapiens]
gi|78070557      Mass: 13900    Score: 93    Queries matched: 1
Hist3h2bb protein [Mus musculus]
```

2.  gi|51467848    Mass: 17035    Score: 24    Queries matched: 1
    PREDICTED: similar to ribosomal protein S26 [Homo sapiens]
    ☐ Check to include this hit in error tolerant search Query  Observed   Mr(expt)   Mr(calc)   Delta  Miss  Score  Expect  Rank  Peptide
      1    1742.8000  1741.7927  1740.8915  0.9012   1    24     1.4     2   K.LHYCVSCAIHNXVVR.N

3.  gi|51468566   Mass: 51117   Score: 22   Queries matched: 1
    PREDICTED: similar to DA508N22.1 (HSPC025) [Homo sapiens]
    ☐ Check to include this hit in error tolerant search

| Query | Observed | Mr(expt) | Mr(calc) | Delta | Miss | Score | Expect | Rank | Peptide |
    |---|---|---|---|---|---|---|---|---|---|
    | 1 | 1742.8000 | 1741.7927 | 1740.9522 | 0.8405 | 1 | 22 | 2.7 | 3 | R.ILSGRRDLFSIELNX.K |

---

4.  gi|456351   Mass: 13035   Score: 21   Queries matched: 1
    ribosomal protein S26 [Homo sapiens]
    ☐ Check to include this hit in error tolerant search

| Query | Observed | Mr(expt) | Mr(calc) | Delta | Miss | Score | Expect | Rank | Peptide |
    |---|---|---|---|---|---|---|---|---|---|
    | 1 | 1742.8000 | 1741.7927 | 1741.9119 | -0.1192 | 1 | 21 | 3 | 4 | K.LHYCVSCVIHSKVVR.N |

Proteins matching the same set of peptides:
    gi|41222070   Mass: 12977   Score: 21   Queries matched: 1
    PREDICTED: similar to 40S ribosomal protein S26 [Homo sapiens]

---

5.  gi|21740102   Mass: 51309   Score: 20   Queries matched: 1
    hypothetical protein [Homo sapiens]
    ☐ Check to include this hit in error tolerant search

| Query | Observed | Mr(expt) | Mr(calc) | Delta | Miss | Score | Expect | Rank | Peptide |
    |---|---|---|---|---|---|---|---|---|---|
    | 1 | 1742.8000 | 1741.7927 | 1741.8522 | -0.0595 | 0 | 20 | 4.1 | 5 | R.HFVAVYDGSSSIENLX.A |

Proteins matching the same set of peptides:
    gi|24041026   Mass: 59354   Score: 20   Queries matched: 1
    neuropilin- and tolloid-like protein 2 precursor [Homo sapiens]
    gi|31974185   Mass: 55605   Score: 20   Queries matched: 1
    hypothetical protein [Homo sapiens]

FIGURE 9 gi|20479382   Mass: 37299   Score: 20   Queries matched: 1
Unknown (protein for IMAGE:6166566) [Homo sapiens]

6.  gi|51475918   Score: 18   Queries matched: 1
    PREDICTED: similar to POM121 membrane glycoprotein-like 1 [Homo sapiens]
    ☐ Check to include this hit in error tolerant search Query  Observed   Mr(expt)   Mr(calc)   Delta  Miss  Score  Expect  Rank  Peptide
      1    1743.8000  1741.7927  1742.8885  -1.0958  1    18    6.6      6   K.AAGLPSNLVPTERCHR.A 7.  gi|4958133   Mass: 4428   Score: 17   Queries matched: 1
    N-Terminal Egf-Like Domain From Human Factor Vii, Nmr, 23 Structures
    ☐ Check to include this hit in error tolerant search Query  Observed   Mr(expt)   Mr(calc)   Delta  Miss  Score  Expect  Rank  Peptide
      1    1742.8000  1741.7927  1742.4294  -0.6367  0    17    7.4      7   -.SDGDQCASSPCQNGGSCR.D Proteins matching the same set of peptides:
    gi|5542232   Mass: 4871   Score: 17   Queries matched: 1
    Chain A, The First Egf-Like Domain From Human Blood Coagulation Fvii (Fucosylated At Ser-60), Nmr, Minimized Average 8.  gi|17223622   Score: 17   Queries matched: 1
    ATP-binding cassette A6 [Homo sapiens]
    ☐ Check to include this hit in error tolerant search Query  Observed   Mr(expt)   Mr(calc)   Delta  Miss  Score  Expect  Rank  Peptide
      1    1742.8000  1741.7927  1740.8431  0.9497   0    17    7.6      8   K.HQNILLEVDDFEHR.N Proteins matching the same set of peptides:
    gi|21756997   Score: 17   Queries matched: 1
    gi|21779824   Score: 17   Queries matched: 1
    gi|27436953   Score: 17   Queries matched: 1

FIGURE 10

9.  gi|28279803    Mass: 24596    Score: 17    Queries matched: 1
    PON2 protein (Homo sapiens)
    ☐ Check to include this hit in error tolerant search Query  Observed  Mr(expt)  Mr(calc)  Delta  Miss Score Expect Rank Peptide
     1     1742.8000 1741.7927 1742.9202 -1.1275  1    17     3    9  K.FEEGENSLLHLKTVK.H 10. gi|15559379    Mass: 33903    Score: 17    Queries matched: 1
    DHRS1 protein (Homo sapiens)
    ☐ Check to include this hit in error tolerant search Query  Observed  Mr(expt)  Mr(calc)  Delta  Miss Score Expect Rank Peptide
     1     1742.8000 1741.7927 1742.9427 -1.1500  1    17     8.4  10 K.AGATVYITGRHLDTLR.V Proteins matching the same set of peptides:
    gi|16196523    Mass: 33859    Score: 17    Queries matched: 1
    DHRS1 protein (Homo sapiens)
    gi|21739562    Mass: 33915    Score: 17    Queries matched: 1
    hypothetical protein (Homo sapiens)
    gi|28193144    Mass: 33837    Score: 17    Queries matched: 1
    unnamed protein product (Homo sapiens)

Search Parameters

Type of search          : MS/MS Ion Search
Enzyme                  : Trypsin
Mass values             : Monoisotopic
Protein Mass            : Unrestricted
Peptide Mass Tolerance  : ± 1.5 Da
Fragment Mass Tolerance : ± 1.5 Da
Max Missed Cleavages    : 1
Instrument type         : MALDI-TOF-PSD
Number of queries       : 1

FIGURE 11

Mascot Search Results

Peptide View

MS/MS Fragmentation of AMGIMNSFVNDIFER
Found in gi|31977, histone H2B [Homo sapiens]

Match to Query 1: 1741.792724 from(1742.800000,1+)
PSD 1742.8
From data file PSD1742.8 20060207.txt Click mouse within plot area to zoom in by factor of two about that point
Or, [Plot from] 100 to 1800 Da

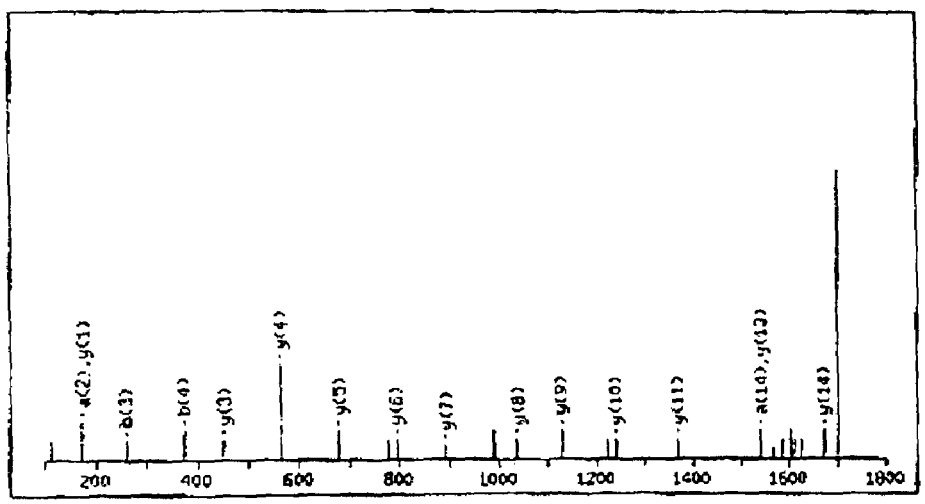

Monoisotopic mass of neutral peptide Mr(calc): 1742.8119
Ions Score: 93 Expect: 2e-07
Matches (Bold Red): 16/91 fragment ions using 20 most intense peaks

| # | Immon. | a | a* | a⁰ | b | b* | b⁰ | Seq. | y | # |
|---|---|---|---|---|---|---|---|---|---|---|
| 1 | 44.0495 | 44.0495 | | | 72.0444 | | | A | | 15 |
| 2 | 104.0528 | 175.0900 | | | 203.0849 | | | M | 1672.7821 | 14 |
| 3 | 30.0338 | 232.1114 | | | 260.1063 | | | G | 1541.7417 | 13 |
| 4 | 86.0964 | 345.1955 | | | 373.1904 | | | I | 1484.7202 | 12 |
| 5 | 104.0528 | 476.2360 | | | 504.2309 | | | M | 1371.6361 | 11 |
| 6 | 87.0553 | 590.2789 | 573.2523 | | 618.2738 | 601.2472 | | N | 1240.5957 | 10 |
| 7 | 60.0444 | 677.3109 | 660.2844 | 659.3003 | 705.3058 | 688.2793 | 687.2953 | S | 1126.5527 | 9 |
| 8 | 120.0808 | 824.3793 | 807.3528 | 806.3688 | 852.3742 | 835.3477 | 834.3637 | F | 1039.5207 | 8 |
| 9 | 72.0808 | 923.4477 | 906.4212 | 905.4372 | 951.4426 | 934.4161 | 933.4321 | V | 892.4523 | 7 |
| 10 | 87.0553 | 1037.4907 | 1020.4641 | 1019.4801 | 1065.4856 | 1048.4590 | 1047.4750 | N | 793.3839 | 6 |
| 11 | 88.0393 | 1152.5176 | 1135.4911 | 1134.5070 | 1180.5125 | 1163.4860 | 1162.5020 | D | 679.3410 | 5 |
| 12 | 86.0964 | 1265.6017 | 1248.5751 | 1247.5911 | 1293.5966 | 1276.5700 | 1275.5860 | I | 564.3140 | 4 |
| 13 | 120.0808 | 1412.6701 | 1395.6435 | 1394.6595 | 1440.6650 | 1423.6384 | 1422.6544 | F | 451.2300 | 3 |
| 14 | 102.0550 | 1541.7127 | 1524.6861 | 1523.7021 | 1569.7076 | 1552.6810 | 1551.6970 | E | 304.1615 | 2 |
| 15 | 129.1135 | | | | | | | R | 175.1190 | 1 |

NCBI BLAST search of AMGIMNSFVNDIFER
(Parameters: blastp, nr protein database, expect=20000, no filter, PAM30)
Other BLAST web gateways

FIGURE 13

{MATRIX SCIENCE} Mascot Search Results

```
User              : PEP
Email             : pevsnori@earthlink.net
Search title      : CID 1621
MS data file      : tubulin CID 1621.txt
Database          : NCBInr 20060203 (3284262 sequences; 1125694017 residues)
Taxonomy          : Mus. (117021 sequences)
Timestamp         : 7 Feb 2006 at 22:32:54 GMT
Significant hits: gi|4507729  tubulin, beta 2 [Homo sapiens]
```

Probability Based Mowse Score

Ions score is $-10*\text{Log}(P)$, where P is the probability that the observed match is a random event.
Individual ions scores > 22 indicate peptides with significant homology.
Individual ions scores > 33 indicate identity or extensive homology ($p<0.05$).
Protein scores are derived from ions scores as a non-probabilistic basis for ranking protein hits.

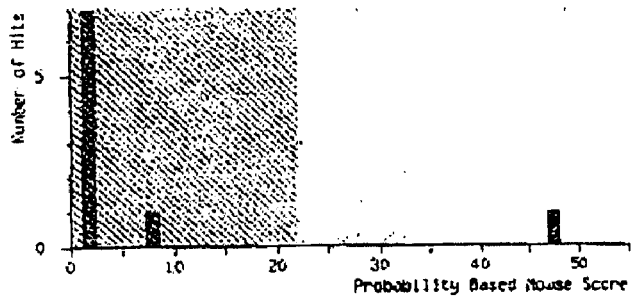

Peptide Summary Report

[Format As] Peptide Summary                                                                Help Significance threshold $p< 0.05$        Max. number of hits 20

FIGURE 14

Standard scoring ⦿ MudPIT scoring ○ Ions score cut-off 0         Show sub-sets ☐
Show pop-ups ⦿ Suppress pop-ups ○ Sort unassigned Decreasing Score   Require bold red ☐

[Select All]  [Select None]  [Search Selected]  ☐ Error tolerant 1.  gi|4507729      Mass: 49875    Score: 47    Queries matched: 1
    tubulin, beta 2 [Homo sapiens]
    ☐ Check to include this hit in error tolerant search Query  Observed   Mr(expt)   Mr(calc)   Delta   Miss  Score  Expect  Rank  Peptide
    ☑  1   1621.0000  1619.9927  1619.8282  0.1645   0    47    0.0022    1   R.LHFFMPGFAPLTSR.G Proteins matching the same set of peptides:
    gi|4580988      Mass: 49639    Score: 47    Queries matched: 1
    class I beta tubulin [Cricetulus griseus]
    gi|12846758     Mass: 49608    Score: 47    Queries matched: 1
    unnamed protein product [Mus musculus]
    gi|12851187     Mass: 49496    Score: 47    Queries matched: 1
    unnamed protein product [Mus musculus]
    gi|13097383     Mass: 33979    Score: 47    Queries matched: 1
    Tubb2a protein [Mus musculus]
    gi|13542680     Mass: 49783    Score: 47    Queries matched: 1
    Tubulin, beta, 2 [Mus musculus]
    gi|15489150     Mass: 49554    Score: 47    Queries matched: 1
    Tubulin, beta 4 [Homo sapiens]
    gi|20746161     Mass: 49921    Score: 47    Queries matched: 1
    tubulin, beta [Mus musculus]
    gi|26355845     Mass: 32239    Score: 47    Queries matched: 1
    unnamed protein product [Mus musculus]
    gi|26355729     Mass: 34173    Score: 47    Queries matched: 1
    unnamed protein product [Mus musculus]
    gi|29126893     Mass: 21440    Score: 47    Queries matched: 1

FIGURE 15

```
Tubb5 protein [Mus musculus]
gi|51710798        Mass: 49754    Score: 47    Queries matched: 1
PREDICTED: similar to tubulin, beta, 2 [Mus musculus]
gi|74141821        Mass: 49667    Score: 47    Queries matched: 1
unnamed protein product [Mus musculus]
gi|74144588        Mass: 49771    Score: 47    Queries matched: 1
unnamed protein product [Mus musculus]
gi|74204140        Mass: 49616    Score: 47    Queries matched: 1
unnamed protein product [Mus musculus]
gi|74323170        Mass: 49889    Score: 47    Queries matched: 1
unnamed protein product [Mus musculus]
gi|74423737        Mass: 49652    Score: 47    Queries matched: 1
unnamed protein product [Mus musculus]
gi|75773583        Mass: 49799    Score: 47    Queries matched: 1
Hypothetical protein LOC539149 [Bos taurus]
gi|82801517        Mass: 49384    Score: 47    Queries matched: 1
PREDICTED: similar to tubulin, beta, 2 [Mus musculus]
```

---

```
2.   gi|74193658        Score: 6      Queries matched: 1
     unnamed protein product [Mus musculus]
     [ ] Check to include this hit in error tolerant search Query  Observed   Mr(expt)   Mr(calc)   Delta  Miss Score Expect Rank Peptide
        1   1621.0000  1619.9927  1619.7977  0.1950   0    6     26    2   R.KPDTQVQIFTPSTR.E
```

---

```
3.   gi|166793418       Score: 3      Queries matched: 1
     zinc finger protein [Mus musculus]
     [ ] Check to include this hit in error tolerant search Query  Observed   Mr(expt)   Mr(calc)   Delta  Miss Score Expect Rank Peptide
        1   1621.0000  1619.9927  1619.7224  0.2703   0    3     55    3   R.FREMMHSCEKPYX.C
```

FIGURE 16

```
    Proteins matching the same set of peptides:
       gi|74205825        Score: 3      Queries matched: 1
─────────────────────────────────────────────────────────────────────────────
4.    gi|1526436         Mass: 7475     Score: 3      Queries matched: 1
      ryanodine receptor type-3 (Mus musculus)
      ☐ Check to include this hit in error tolerant search Query  Observed    Mr(expt)   Mr(calc)   Delta   Miss  Score  Expect  Rank  Peptide
        1    1621.0000   1619.9927  1619.7426  0.2501   0      3      56     4   M.AEAGEGGEDEIQFLR.T ─────────────────────────────────────────────────────────────────────────────
5.    gi|23271723        Score: 3      Queries matched: 1
      3110050K21Rik protein (Mus musculus)
      ☐ Check to include this hit in error tolerant search Query  Observed    Mr(expt)   Mr(calc)   Delta   Miss  Score  Expect  Rank  Peptide
        1    1621.0000   1619.9927  1619.7647  0.2280   1      3      63     5   K.EERASLLSDLGPCCK.A Proteins matching the same set of peptides:
       gi|61742810        Score: 3      Queries matched: 1
─────────────────────────────────────────────────────────────────────────────
6.    gi|29743065        Score: 2      Queries matched: 1
      Inadl protein (Mus musculus)
      ☐ Check to include this hit in error tolerant search Query  Observed    Mr(expt)   Mr(calc)   Delta   Miss  Score  Expect  Rank  Peptide
        1    1621.0000   1619.9927  1619.7903  0.2024   1      2      68     6   R.KTSLSASPFEHSSSR.E Proteins matching the same set of peptides:
       gi|55769578        Score: 2      Queries matched: 1
       gi|55769581        Score: 2      Queries matched: 1
       gi|74190803        Score: 2      Queries matched: 1
       gi|74193692        Score: 2      Queries matched: 1
```

FIGURE 17

7.  gi|29302251       Score: 2        Queries matched: 1
    Meiosis-specific nuclear structural protein 1 (Mus musculus)
    ☐ Check to include this hit in error tolerant search Query   Observed   Mr(expt)   Mr(calc)   Delta   Miss   Score   Expect   Rank   Peptide
      1     1621.0000  1619.9927  1619.8042  0.1885   0      2       69      7     R.QELYQESQAEIIK.L 8.  gi|56238155       Score: 2        Queries matched: 1
    novel protein (Mus musculus)
    ☐ Check to include this hit in error tolerant search Query   Observed   Mr(expt)   Mr(calc)   Delta   Miss   Score   Expect   Rank   Peptide
      1     1621.0000  1619.9927  1619.9035  0.0893   0      2       74      8     K.IGTSTLLFLVGAWSR.A Proteins matching the same set of peptides:
    gi|74142573       Score: 2        Queries matched: 1

9.  gi|134335594      Score: 2        Queries matched: 1
    RNA binding motif protein 10 (Mus musculus)
    ☐ Check to include this hit in error tolerant search Query   Observed   Mr(expt)   Mr(calc)   Delta   Miss   Score   Expect   Rank   Peptide
      1     1621.0000  1619.9927  1619.7911  0.2016   1      2       76      9     R.MLQAMGWKEGSGLGR.K Proteins matching the same set of peptides:
    gi|126354250      Score: 2        Queries matched: 1
    gi|139104982      Score: 2        Queries matched: 1
    gi|74148832       Score: 2        Queries matched: 1
    gi|74198465       Score: 2        Queries matched: 1
    gi|74219366       Score: 2        Queries matched: 1
    gi|82795831       Score: 2        Queries matched: 1
    gi|82795833       Score: 2        Queries matched: 1
    gi|82795835       Score: 2        Queries matched: 1

FIGURE 18

| | | |
|---|---|---|
| gi|82878000 | Score: 2 | Queries matched: 1 |
| gi|82878803 | Score: 2 | Queries matched: 1 |
| gi|76146659 | Score: 0 | Queries matched: 1 |

Search Parameters

| | |
|---|---|
| Type of search | : MS/MS Ion Search |
| Enzyme | : Trypsin |
| Mass values | : Monoisotopic |
| Protein Mass | : Unrestricted |
| Peptide Mass Tolerance | : ± 0.5 Da |
| Fragment Mass Tolerance | : ± 0.8 Da |
| Max Missed Cleavages | : 1 |
| Instrument type | : MALDI-QUAD-TOF |
| Number of queries | : 1 |

Mascot: http://www.matrixscience.com/

METHODS FOR DIRECT BIOMOLECULE IDENTIFICATION BY MATRIX-ASSISTED LASER DESORPTION IONIZATION (MALDI) MASS SPECTROMETRY

CROSS-REFERENCE TO RELATED APPLICATIONS

The present application is a non-provisional application claiming the priority of copending provisional applications U.S. Ser. No. 60/722,206, filed Sep. 30, 2005, and U.S. Ser. No. 60/784,016, filed Mar. 20, 2006, the disclosures of which are incorporated by reference herein in their entireties. Applicants claim the benefits of these applications under 35 U.S.C. sctn. 119 (e).

FIELD OF THE INVENTION

The present invention relates generally to methods for the in situ determination of the types and amount of proteins in a tissue sample by direct tissue matrix associated laser desorption ionization imaging time-of-flight (DT-MALDI-TOF) measurement. The methods allow for direct analysis of tissue samples, without the need for protein extraction and analysis of protein content of the tissue sample by other standard methods, e.g. electrophoretic analysis or other cumbersome or time consuming methods. The methods also allow for the rapid and accurate detection of particular biological molecules in normal and diseased tissue, and also for determining a subject's response to particular therapies.

BACKGROUND OF THE INVENTION

Time of flight mass spectrometry from gel isolates or chromatographic columns are accepted means of identifying proteins based on mass and charge (m/z). In 1988, Koichi Tanaka reported that laser irradiation of a mixture of methanol-ethylene glycol-cobalt ultra fine powder (Co UFT) transferred energy to proteins, chymotrypsinogen and lysozyme, generating a vapor/ion-phase of intact macro molecules that could be detected by time of flight (TOF) mass spectrometry (Tanaka, et al., *Rapid Commun. Mass Spectrom.* 1988, 2, 151-153). This demonstration paved the way for using laser desorption ionization mass spectrometry on solid tissue, direct tissue MALDI (DT-MALDI).

MALDI (TOF) identifies proteins and peptides as mass charge (m/z) spectral peaks. Further advances, post-source decay (MALDI-PSD) and collision-induced dissociation (MALDI-CID), have become standard methods to identify proteins from cell or tissue homogenates that are responsible for these peaks. (Hansen, et al., *Molecular & Cellular Proteomics* 2003, 2, 299-314; Norris, et al. *Anal Chem.* 2003, 75, 6642-6647; Zhang, et al., *Am Soc Mass Spectrom* 2003, 14, 1012-1021; Wang, et al. *Journal of Proteome Research* 2005, 4, 2397-2403; Vasilescu, et al., *Journal of Proteome Research* 2005, 4, 2192-2200; Vandermoere, et al., *Oncogene* 2005, 24, 5482-5491; Luo, et al., *Molecular Biotechnology* 2005, 29, 233-244; Le Guezennec, et al., *Molecular and Cellular Biology* 2006, 26, 843-851. However, most of these procedures utilize harsh digestion conditions and protein extraction procedures prior to analysis by MALDI-TOF methods. Matrices have evolved to include small organic molecules and heavy metals that can be applied to or mixed with the analyte (Tanaka, et al., *Rapid Commun. Mass Spectrom.* 1988, 2, 151-153). The most often used matrices absorb light at 337%, the wavelength of a nitrogen laser, and thereby facilitate desorption and ionization of adjacent biological materials.

Ions of the same charge acquire a similar kinetic energy; however, their velocity in the ion chamber depends on their respective masses. The ion time of travel to an anode is measured, precisely by the detector and is recorded as a time-mass/charge spectrum with peaks representing proteins in the sample. Based on instrument calibration of standard samples, these values are converted to mass values for National Center for Biotechnology Information (NCBI) database analysis of peptide fragments with Mascot©, and Blast© software. Protein m/z Spectra can be obtained from fluids, cells and tissues of matrix coated protein extraction preparations with Maldi tof and Maldi tof tof. Although protein signature peaks are reported (Norris, et al., *Analytical Chemistry* 2003, 75, 6642-6647), there have been no reports of proteins identified directly from cells or tissue using these technologies. Thus, there is a need in the art to provide a more rapid, yet accurate method to identify proteins directly from a tissue sample without a need for further protein extraction of the sample to be followed by protein determination using standard methods such as 1D, 2D or capillary electrophoresis. These needs are addressed by the agents and methods of the present invention.

All publications, patent applications, patents and other reference material mentioned are incorporated by reference in their entirety. In addition, the materials, methods and examples are only illustrative and are not intended to be limiting. The citation of references herein shall not be construed as an admission that such is prior art to the present invention.

SUMMARY OF THE INVENTION

In its broadest aspect, the invention provides a method for analyzing the biological molecule content of a tissue or cell in situ, for example, the protein content of a tissue or cell in situ, comprising the use of direct tissue matrix assisted laser desorption ionization imaging time-of flight (DT-MALDI-TOF) measurements, without extracting the proteins from the tissues or cells, whereby such method may disrupt the cellular or tissue architecture and may lead to the production of artifacts, depending on the extraction method used. Particular cell or tissue disruption procedures that result in the production of artifacts include, but are not limited to, procedures such as homogenization, or sonication, or freezing the cells or tissues without first fixing the cells or tissues in a gentle fixative, such as an alcohol, as described herein. These harsh methods of extracting the biological molecule content of a cell or tissue are not utilized by the methods of the present invention. Accordingly, the procedures described herein eliminate the need for such harmful and cell or tissue disruptive extraction methods, and also saves the time needed for carrying out such additional steps, while at the same time diminishing the artifacts observed when such harsh extraction procedures are utilized. More particularly, the invention provides a method to characterize, identify and quantify biological molecules in a mixture without adulterating the results due to freezing (without fixing first), or disrupting the cells by an extraction procedure such as homogenization or sonication or through use of a tissue grinder and sieving mechanism. The biological molecules may be selected from proteins or peptides or fragments thereof, nucleic acids, carbohydrates, lipids, lipoproteins, and the like. The method of the present invention utilizes mass spectrometry for characterization of the accurate mass of a plurality of biological molecules in a mixture, particularly wherein a majority of said biological molecules is characterized, such that a majority of the mixture's components may be identified and/or quantitated. Accordingly, the methods described herein are useful for the diagnosis of a disease or medical condition, and when used alone, or combined with, for example, histological procedures, results in the identification of biomarkers of particular diseases. Such biomarkers may be identified in body cells, or tissues, or may be present in body fluids, such as whole blood, or serum, or plasma, or urine, or cerebrospinal fluid, and the like. In another broad aspect of the invention, the methods and procedures described may be used to follow the cell or tissue distribution of a new chemical entity or therapeutic agent, for which cell or tissue distribution is unknown. For example, the therapeutic agent may be a small organic molecule (synthetic or naturally derived), or a biological molecule used for treating a disease or condition, such as a small interfering nucleic acid molecule, wherein it may be desirable to track its bodily disposition and/or excretion rate, for example. Such a method can then be used in a pre-clinical or clinical setting in order to do, for example, ADME (Absorption, Distribution, Metabolism and Excretion) studies, or toxicity studies.

Accordingly, a first aspect of the invention provides a method for analyzing the biological molecule content of a tissue sample in situ, comprising:

a) collecting a sample from a subject into a first solution capable of maintaining integrity of the biological molecule;

b) treating the sample with a second solution comprising one or more enzymes, or chemicals, capable of dissociating the tissue sample or of digesting the dissociated tissue sample into smaller fragments;

c) treating the preparation from step b) with a matrix assisted laser desorption ionization imaging (MALDI) matrix solution; and d) analyzing the preparation from step c) by direct tissue (DT)-matrix assisted laser desorption ionization imaging (MALDI)-time of flight (TOF) measurement or DT-MALDI-TOF-TOF measurement;

e) creating a data file utilizing the information from step d);

f) entering the data from the data file of step e) into an external database to create a signature map for the tissue from which the data was obtained; and g) comparing the results from step d) with a signature map for normal tissue, wherein said normal tissue corresponds to, or is of the same tissue type, as the tissue from which the sample was obtained.

In another particular aspect, the method provides for an additional step whereby the tissue or cell sample is analyzed by histological means, in order to compare the results to that obtained by DT-MALDI-TOF measurements. Once confirmation of the findings is obtained, preferably after the results have been validated at least three times using both the DT-MALDI-TOF measurement and the histological analysis, and the data is entered into a data file, this histological step may be omitted in future analyses and the biological molecule assessment made using DT-MALDI-TOF alone.

In one embodiment, the biological molecule is selected from the group consisting of a protein, a peptide, or fragments thereof, a nucleic acid, including both DNA and RNA, an oligonucleotide or polynucleotide, an antisense molecule, a small interfering nucleic acid molecule, such as a siRNA or shRNA, a carbohydrate, a lipid, a lipoprotein and the like. In another particular embodiment, the chemical used for dissociation of the tissue or cells is formic acid or cyanogen bromide. In another embodiment, the method may be used to study the disposition of a new chemical entity (NCE), such as a small organic molecule (synthetic or naturally derived), or new biological entity (NBE) in vitro or in vivo, whereby pre-clinical or clinical studies are necessary prior to FDA approval of a new chemical or biological entity for therapeutic use. In this manner, the methods of the present invention may be used to track the location of the NCE or NBE in vitro eg. within the cell or tissue. Alternatively, the methods of the present invention may be used to track the disposition of the NCE or NBE within the body, thus providing a new means to perform ADME studies (Absorption, Distribution, Metabolism and Excretion). In another embodiment, the methods of the present invention may prove useful when it is of interest in determining whether two or more therapeutics agents, when delivered to a cell, tissue or organ, result in a toxic effect on the cell. Accordingly, the methods of the present invention allow for potentially determining whether the use of two or more therapeutic agents may be contraindicated, based on the presence or absence of particular biomarkers after administration of the two or more therapeutic agents to a subject. Once such an effect is realized, an in vitro screen may be developed that could assess such an effect on particular cells, or tissues in culture. Thus, in vitro screening for potential toxic profiling of drugs may be envisioned using the methods of the present invention.

In one particular embodiment, the mass of enzymatically, or chemically, derived biological molecules is preferably measured or determined to an accuracy of 10 attamols, most preferably to an accuracy of 5 attamols, and particularly preferred to an accuracy of 1 attamol.

In another particular embodiment, the tissue or cell sample is prepared using an ultra cryomicrotome. In yet another particular embodiment, the tissue or cell preparation is prepared to allow for resolution of structures at the subcellular level. In yet another particular embodiment, the tissue or cell preparations are sectioned by a microtome to allow for resolution of cell or tissue structures in the range from about 0.05 micron to about 2.0 microns. In yet another particular embodiment, the tissue or cell preparations are sectioned by a microtome to allow for resolution of cell or tissue structures in the range from about 0.1 micron to about 1.5 micron. In yet another particular embodiment, the tissue or cell preparations are sectioned by a microtome to allow for resolution of cell or tissue structures in the range from about 0.5 micron to about 1.0 micron.

In another particular embodiment, mass spectrometry may be accomplished by any recognized mass spectrometry method, from a single or tandem mass spectrometer device. The single mass spectrometer may be one of a matrix assisted laser desorption ionization time-of-flight mass spectrometer, electrospray time-of-flight mass spectrometer. The tandem mass spectrometer may be one of a Fourier-transform cyclotron resonance mass spectrometer, an electrospray quadrupole time-of-flight mass spectrometer, a tandem time-of-flight mass spectrometer, a quadrupole ion trap mass spectrometer, and a triple quadrupole mass spectrometer to name only a few.

In another particular embodiment, the method provides for both qualitative identification of the proteins in the sample, as well as, a quantitative measurement of the proteins in the sample.

In another particular embodiment, the method provides for a level of detection of a protein in a sample in an amount of about 10 attamols, most preferably of about 5 attamols, and particularly preferred of about 1 attamol. As used herein, the term "about" refers to approximately or close to, usually within (i.e., ±) 10% of the given value or quantity.

In another particular embodiment, an internal standard is incorporated to provide a means for quantitating the abundance of a protein or peptide, thereby accomplishing absolute quantitation of a protein or peptide in a sample. Relative quantitation of protein/peptide abundances in complex mixtures is accomplished by comparing ion maps generated in different conditions (i.e diseased vs. non-diseased, treated vs. non-treated).

In another particular embodiment, a control, or controls of known concentration are included and placed adjacent to the test sample prior to mass spectrometric analysis. In a preferred aspect, the control will be equimolar. In a particular embodiment, the addition of the control(s) will allow for quantitation of the identified proteins.

In yet another particular embodiment, the sample may be collected into a collection device, wherein the collection device is selected from the group consisting of a microcapillary pipette, a plastic or glass tube, and a slide for a cellular or tissue sample obtained from a microtime or an ultra cryo microtome.

In yet another particular embodiment, the first solution is a buffered solution or an alcohol.

In yet another particular embodiment, the buffered solution is selected from the group consisting of phosphate buffered saline (PBS), a phosphate buffer, a potassium buffer, a choline buffer and a glycine buffer.

In yet another particular embodiment, the alcohol is selected from the group consisting of methanol, ethanol, propanol, butanol, isopropyl alcohol and isobutanol.

In yet another particular embodiment, the one or more enzymes capable of dissociating the tissue and degrading the tissue into peptide fragments are selected from the group consisting of a collagenase, a lipase and a protease.

In a more particular embodiment, the one or more enzymes may be selected from the group consisting of trypsin, endoprotease-LysC, endoprotease-ArgC, endoprotease-GluC, and chymotrypsin, to name only a few. In another more particular embodiment, the chemical utilized can be cyanogen bromide, or formic acid.

In yet another particular embodiment, the one or more enzymes are left in contact for a time and at a temperature sufficient to obtain dissociated tissue and peptide fragments. For example, the time sufficient to obtain dissociated tissue or peptide fragments may range from about 10 minutes to about 2 hours, and in certain cases may range up to about 24 hours. The length of time is dependent upon the type of tissue, the tissue thickness, the temperature used, and the enzyme or chemical used. In yet another particular embodiment, the temperature ranges from about 20° C. to about 60° C.

In another embodiment, the peptides identified through use of the methods of the invention are matched to known peptides having the same atomic mass using Mascot©. Alternatively, they may be identified using a BLAST analysis, the procedure of which is known to those skilled in the art. In another embodiment of the invention, the database of sequences is a database of amino acid sequences of a plurality of proteins. In a further embodiment, the database of sequences is a nucleotide database. Examples of such databases include the National Center for Biological Information (NCBI) database (Pub Med or GenBank), the Human Genome Project (HGP), and PDB (Protein Data Bank). In another particular embodiment, the nucleic acids or proteins identified in a tissue or cellular sample may be compared to any one or more sequences identified by gene chip analysis, such as those provided by Affymetrix. On the other hand, if one desired to compare the tissue or cellular disposition of an unknown drug or therapeutic agent with a known compound, such libraries of compounds may be used. Examples of libraries of compounds that are commercially available include the Available Chemicals Directory (ACD,) the Specs and Bio-Specs database, the Maybridge database, and the Chembridge database.

In another embodiment, the protein(s) molecular weight, net charge, and mass to name only a few from the plurality of sequences are stored for comparison with experimentally derived protein molecular weights, net charges and mass.

The present invention also provides a database of characterized biological components in a mixture, wherein the biological components are described by their ion map, including accurate mass and molecular weight and net charge of the protein or fragments thereof. In particular, the mixture may be described by one or more features including organism, organ source, tissue source, cellular source, treatment conditions, disease condition, etc.

In yet another particular embodiment, the MALDI matrix is selected from the group consisting of $\alpha$.-4 cyano hydroxy-cinnamic acid (CHCA), sinnapinic acid, p-nitroaniline, a heavy metal and glycerol.

In yet another particular embodiment, the tissue sample is obtained from normal tissue, or abnormal/diseased tissue.

In yet another particular embodiment, the diseased tissue is a tumor tissue, tissue from a hyperproliferative disorder other than cancer, or an ischemic tissue.

In yet another particular embodiment, the hyperproliferative disorder other than cancer is selected from the group consisting of rheumatoid arthritis, lupus, multiple sclerosis, psoriasis and other inflammatory or autoimmune diseases.

In yet another particular embodiment, the tumor tissue is obtained from a benign tumor or a malignant tumor.

In yet another particular embodiment, the ischemic tissue is obtained from the brain, spinal cord or other nervous system tissue.

In yet another particular embodiment, the ischemic tissue is obtained from the heart, brain, spinal cord, kidney, liver, or intestinal tract.

In yet another particular embodiment, the normal or abnormal/diseased tissue is selected from the group consisting of solid tissue or non-solid tissue.

In yet another particular embodiment, the solid tissue is selected from the group consisting of nervous system tissue, cardiac tissue, breast tissue, lung tissue, bladder tissue, gastrointestinal tissue, eyes, bone and tissue from any solid tumor.

In yet another particular embodiment, the non-solid tissue is selected from the group consisting of whole blood or isolated blood cells. In yet another particular embodiment, the isolated blood cells are red blood cells or white blood cells. In yet another particular embodiment, the white blood cells are selected from the group consisting of lymphocytes, polymorphonuclear cells (PMNs), monocytes and macrophages.

A second aspect of the invention provides a method for identifying the presence of abnormal or diseased tissue in a subject comprising:

a) collecting at least two different tissue samples, one of which is obtained from an area suspected of being diseased or abnormal and the second being normal tissue of the same tissue type;

b) treating the tissue samples with a solution of one or more enzymes, or chemicals capable of dissociating the tissue sample and of digesting the dissociated tissue into fragments;

c) treating the preparation from step b) with a MALDI matrix solution; and d) analyzing the preparation from step c) by DT-MALDI-TOF measurement or DT-MALDI-TOF-TOF measurement, wherein the analyzing comprises comparing the biological molecule content of the at least two different tissue samples, and wherein the biological molecule content of the at least two different tissue samples is compared to a signature map for normal tissue or abnormal or diseased tissue of the same tissue type.

In one particular embodiment, the signature map of the normal or diseased tissue is obtained from a pre-determined standard or from a known database of proteins isolated and characterized for that tissue and the specific disease of which the subject is suspected of having or at risk for developing.

A third aspect of the invention provides a method for identifying the extent of tumor cell extravasation comprising:

a) collecting two or more contiguous tissue samples from a tumor mass and the surrounding tissue;

b) treating the tissue samples with a solution of one or more enzymes or chemicals capable of digesting the tissue into fragments;

c) treating the preparation from step b) with a MALDI matrix solution; and d) analyzing the preparation from step c) by DT-MALDI-TOF measurement or DT-MALDI-TOF-TOF measurement, wherein the analyzing comprises comparing the biological molecule content of the two or more contiguous tissue samples, wherein the biological molecule content of the two or more contiguous tissue samples is compared to a signature map for normal tissue or abnormal or diseased tissue of the same tissue type.

A fourth aspect of the invention provides a method for analyzing the protein content of a cell or bodily fluid sample in situ, comprising:

a) collecting a cell or body fluid sample from a subject into a collection device containing a first solution capable of maintaining protein integrity;

b) treating the sample with a second solution comprising one or more enzymes capable of digesting the sample into peptide fragments;

c) treating the preparation from step b) with a matrix assisted laser desorption ionization imaging (MALDI) matrix solution; and d) analyzing the preparation from step c) by direct tissue (DT)-matrix assisted laser desorption ionization imaging (MALDI)-time of flight (TOF) measurement.

e) comparing the results from step d) with a signature map for normal cells or bodily fluid.

In another particular embodiment, the cell or body fluid is selected from the group consisting of urine, serum, plasma, cerebrospinal fluid (CSF), sputum, bone marrow, amniotic fluid, and bronchial lavage.

A fifth aspect of the invention provides a method for determining the presence of a disease in a subject, or for assessing a subject's risk for developing said disease, or for determining a subject's response to a particular therapy for said disease, or for distinguishing between a responder or a non-responder for a particular therapy, the method comprising:

a) collecting a first tissue sample from a subject suspected of having a disease or being at risk for developing a disease or being treated for a disease;

b) collecting a second cellular or body fluid sample from the same subject;

c) treating the first tissue sample with a solution comprising one or more enzymes or chemicals capable of digesting the tissue sample into fragments and treating the second cellular or bodily fluid sample with a solution comprising one or more enzymes or chemicals capable of digesting the sample into peptide fragments;

d) treating the first tissue sample and the second cellular or bodily fluid sample preparations from step c) with a matrix assisted laser desorption ionization imaging (MALDI) matrix solution; and e) analyzing the preparations from step c) by direct tissue (DT)-matrix assisted laser desorption ionization imaging (MALDI)-time of flight (TOF) measurement or DT-MALDI-TOF-TOF measurement;

f) comparing the results from step e) with a signature map for normal tissue, wherein said normal tissue corresponds to the tissue from which the first tissue sample was obtained, and a signature map for normal cells or body fluid, wherein the normal cells or bodily fluid correspond to the cells or body fluid sample obtained from the subject suspected of having or being at risk for developing said disease, or being treated for said disease.

In one particular embodiment, the diseases are selected from the group consisting of breast cancer, colon cancer, liver cancer, lung cancer, pancreatic cancer, prostate cancer, gastrointestinal cancer, uterine cancer, cervical cancer, hepatitis and HIV.

In another particular embodiment, the biological molecule may be a viral protein, such as, but not limited to those associated with hepatitis virus, human immunodeficiency virus, or human papilloma virus.

In yet another particular embodiment, the methods may be used to monitor the effectiveness of therapies by assessing the presence or absence of certain proteins, such as for example, certain tumor antigens such as those noted above. If a therapy is effective, the tumor antigen may decrease in level, whereas if the therapy is not effective, the tumor antigen may show no change or may increase in level.

In yet another particular embodiment, the methods of the invention may also be used to assess whether a subject, or a cell, is a "responder" or a "non-responder" as relates to certain therapies or treatments. For example, one may assess whether a subject or a cell is a responder by observing a change for example, a receptor molecule, such as an estrogen receptor, whereby the subject or cell is being treated using a selective estrogen receptor modulator or SERM. A decrease in the growth or proliferation of a tumor cell in vitro or in vivo bearing such estrogen receptor indicates that the subject or cell is responding to such therapy. On the other hand, if a subject or cell is a "non-responder", one might expect to see no change in proliferation of such a cell bearing the estrogen receptor or one might expect that there actually may be an increase in the number of cells bearing the estrogen receptor. The term "responder", while it may generally refer to a positive outcome, may also take on a more negative connotation when one is looking at, for example, an untoward reaction or "response" to a drug, such as is often seen in adverse reactions to certain therapies. Thus, a "responder" in this case refers to a person who has responded negatively to a particular therapy. Thus, if a person responds negatively to a drug, the methods of the invention may also be used to identify particular biomarkers that reflect this type of negative response, and this newly identified biomarker can be applied in the future to monitor the response of other patients to such therapy.

A sixth aspect of the invention provides a method for determining the disposition of a new chemical entity or new biological entity in a cell or tissue in situ. In one embodiment, the method comprises:

a) collecting a sample of a tissue or cell from a subject into a first solution capable of maintaining integrity of the tissue or cell sample, prior to treating the subject with a new chemical entity or new biological entity;

b) administering a new chemical entity or new biological entity to a subject;

c) collecting a series of tissue or cell samples from the subject into a first solution capable of maintaining integrity of the tissue or cell sample at various time points after administering the new chemical entity or new biological entity;

d) treating the samples with a second solution comprising one or more enzymes, or chemicals, capable of dissociating the tissue sample or of digesting the dissociated tissue sample into smaller fragments;

e) treating the preparation from step d) with a matrix assisted laser desorption ionization imaging (MALDI) matrix solution; and f) analyzing the preparation from step e) by direct tissue (DT)-matrix assisted laser desorption ionization imaging (MALDI)-time of flight (TOF) measurement or DT-MALDI-TOF-TOF measurement; and g) comparing the results from step f) with a series of tissue or cell samples, comparable to the tissue or cell samples collected from the subject, to which has been added either the new chemical entity or new biological entity;

h) obtaining a signature map or profile for the new chemical or new biological entity in the series of tissue or cell samples for monitoring the presence or absence of the new chemical entity or new biological entity in the same type of tissue or cell sample from the patient, and i) determining the presence and/or amount of the new chemical entity or new biological entity in said tissue or cell samples.

In yet another embodiment, the method comprises:

a) collecting a sample of a tissue or cell from a first subject into a first solution capable of maintaining integrity of the tissue or cell sample, prior to treating the first subject with a new chemical entity or new biological entity;

b) administering a new chemical entity or new biological entity to said first subject;

c) collecting a series of tissue or cell samples from the first subject into a first solution capable of maintaining integrity of the tissue or cell sample at various time points after administering the new chemical entity or new biological entity;

d) treating the samples with a second solution comprising one or more enzymes, or chemicals, capable of digesting the tissue sample into smaller fragments;

e) treating the preparation from step d) with a matrix assisted laser desorption ionization imaging (MALDI) matrix solution; and f) analyzing the preparation from step e) by direct tissue (DT)-matrix assisted laser desorption ionization imaging (MALDI)-time of flight (TOF) measurement or DT-MALDI-TOF-TOF measurement; and g) comparing the results from step f) with a series of tissue or cell samples collected from a second subject, wherein said second subject has not been administered the new chemical entity or new biological entity, wherein the tissue or cell samples collected from the second subject are identical or comparable to the tissue or cell sample collected from the first subject;

h) obtaining a signature map or profile for the new chemical or new biological entity in the series of tissue or cell samples for monitoring the presence or absence of the new chemical entity or new biological entity in the same type of tissue or cell sample from any other subject to be treated in the future with the new chemical entity or new biological entity.

In yet another embodiment, the method may be used for drug development purposes, using either primary cells obtained from a subject or using established cell lines in tissue culture. Through use of the methods of the invention, one may be able to not only identify the disposition of the drug within the cell, but also may be able to identify changes in the MALDI-profile of treated cells. For example, one may detect changes in the protein expression pattern resulting from treating the cells with a new drug or biological entity. In order to determine the location of the drug in particular cells or cell compartments, the method comprises:

a) collecting a cell sample, prior to treating the sample with a new chemical entity or new biological entity, into a solution capable of maintaining cellular integrity;

b) treating said cell sample with a new chemical entity or new biological entity;

c) treating the cell sample from step a) or b) with a second solution comprising one or more enzymes, or chemicals, capable of digesting the cell samples into smaller fragments;

d) treating the samples from step c) with a matrix assisted laser desorption ionization imaging (MALDI) matrix solution; and e) analyzing the preparation from step d) by direct tissue (DT)-matrix assisted laser desorption ionization imaging (MALDI)-time of flight (TOF) measurement or DT-MALDI-TOF-TOF measurement; and f) comparing the results from step b) with the results from step a) to determine the presence of the new chemical entity or new biological entity in the cell sample from step b).

Other aspects and advantages will become apparent from a review of the ensuing detailed description taken in conjunction with the following illustrative drawings.

BRIEF DESCRIPTION OF THE DRAWINGS

FIGS. 3A-3B: Mass spectrum of Maldi TOF analysis of lesioned (b) and non lesioned (a) cerebral hemispheres. The spectral peak intensities of the 33 kDa and 43 kDa proteins are the same in both hemispheres. The color marked 65 kDa protein spectral intensity varies with the size of the lesion. It is least in the normal ipsilateral cingulate gyrus region of the lesioned hemisphere (b) and in the non lesioned hemisphere (a). The color marked spectra from the stroke correspond to the colored number overlying the sampled loci in the photomicrograph.

FIG. 5 provides the results of a histone H2B detailed Mascot search.

FIG. 6 provides the results of a histone H2B detailed Mascot search.

FIG. 7 provides the results of a histone H2B detailed Mascot search.

FIG. 8 provides the results of a histone H2B detailed Mascot search.

FIG. 9 provides the results of a histone H2B detailed Mascot search.

FIG. 10 provides the results of a histone H2B detailed Mascot search.

FIG. 11 provides the results of a histone H2B Mascot peptide analysis.

FIG. 13 provides the results of a stroke model tubulin detailed Mascot search.

FIG. 14 provides the results of a stroke model tubulin detailed Mascot search.

FIG. 15 provides the results of a stroke model tubulin detailed Mascot search.

FIG. 16 provides the results of a stroke model tubulin detailed Mascot search.

FIG. 17 provides the results of a stroke model tubulin detailed Mascot search.

FIG. 18 provides the results of a stroke model tubulin detailed Mascot search.

DETAILED DESCRIPTION OF THE INVENTION

Figure 1:
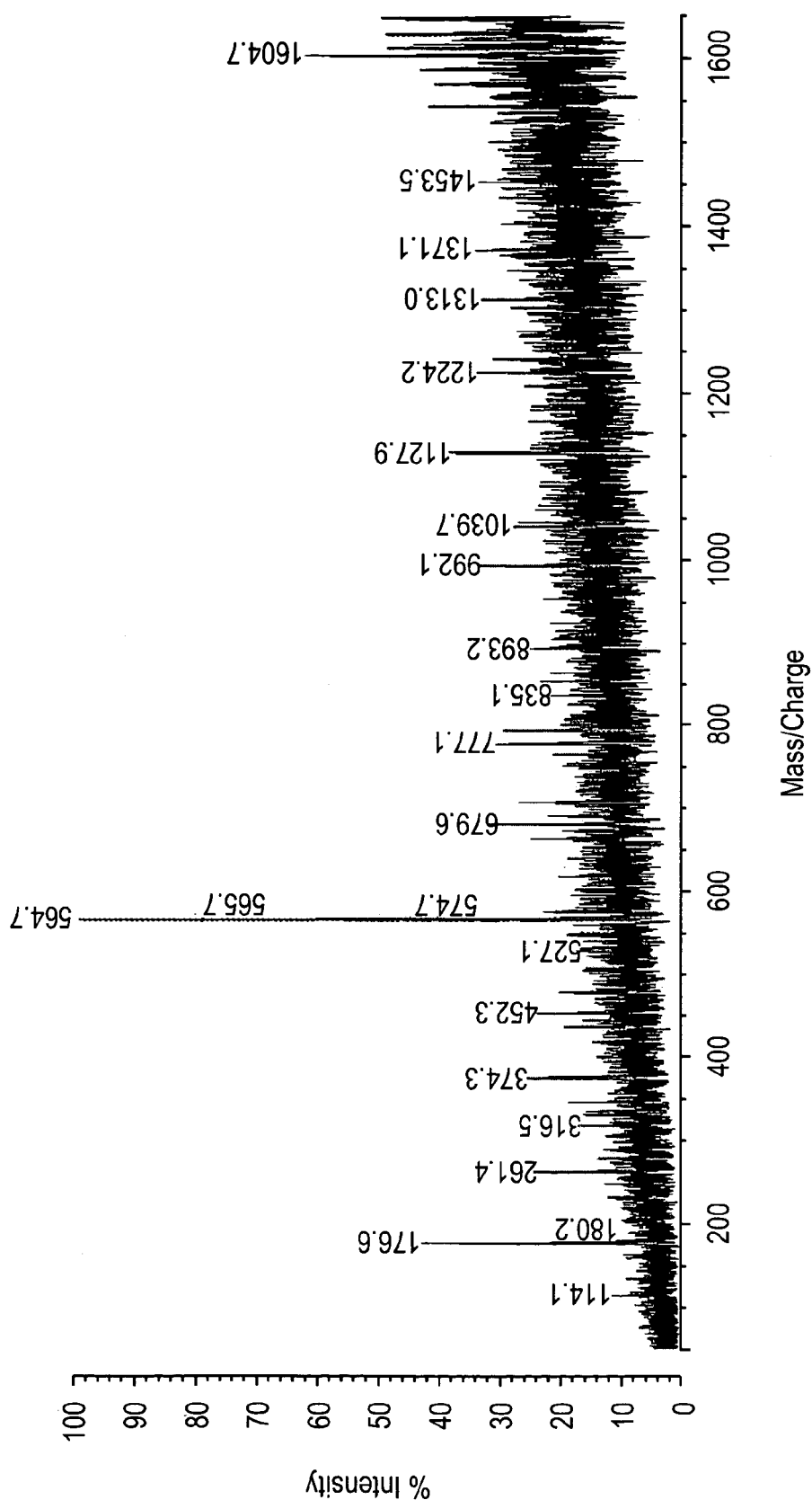
FIG. 1. T47D breast cancer cell Histone H2B Mass spectrum of Maldi PSD fragmentation peptides from precursor ion AMGIMNSFVNDIFER, (SEQ. ID. NO.1) mass 1742.8.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

DEFINITIONS

The terms used herein have the meanings recognized and known to those of skill in the art, however, for convenience and completeness, particular terms and their meanings are set forth below.

A bioinformatics system is utilized to identify the differences in patterns of biological molecules, for example, polypeptide patterns, in the case and control samples. Patterns can be composed of the relative representation of numerous biological molecules (e.g., polypeptides, small molecules, etc.), the collective profile of which is more important than the presence or absence of any specific entities. By identifying patterns in blood or other patient samples, the methods herein do not only provide the window to the presence of disease and other pathology in some embodiments, but also to the body's ongoing response to the disease or pathologic condition in other embodiments. In a high throughput mode (pipelined system operation), data from a first sample are evaluated in a bio-informatics system at the same time another sample is being processed in a detection device using, for example, a mass spectrometry system.

The patterns of biological molecules, eg. polypeptides, present in a sample may be used to identify the disease state of a patient sample in, for example, a diagnostic setting. Samples can be whole blood samples, serum or plasma samples, as well as tissue or bodily fluid samples from a variety of sources that can be used in alternative embodiments. Preferably, though not necessarily, the system used in the diagnostic application is based upon the same technology platform as the platform used to identify the patterns in the first instance. For example, if the platform used to identify the patterns in the first instance is a time of flight (TOF) mass spectrometer, it is preferred that the diagnostic applications of the patterns are run on a time of flight mass spectrometer.

The terms "MALDI" and "MALDI-MS" are used interchangeably and refer to matrix assisted laser desorption imaging and matrix assisted laser desorption/ionization mass spectrometry, which entails methods of mass spectrometric analysis which use a laser as a means to desorb, volatize, and ionize an analyte. In MALDI-MS methods, the analyte is contacted with a matrix material to prepare the analyte for analysis. The matrix material absorbs energy from the laser and transfers the energy to the analyte to desorb, volatize, and ionize the analyte, thereby producing ions from the analyte that are then analyzed in the mass spectrometer to yield information about the analyte. "DT-MALDI TOF" refers to direct tissue MALDI time of flight whereby the MALDI procedure is applied directly to a tissue sample, without the need for further extraction of the biological molecule(s) by harsh methods that disrupt the integrity of the tissue or cell. Such methods include homogenization, or sonication to name just a few. "DT-MALDI" or "DT-MALDI-TOF" or "DT-MALDI-TOF-TOF" allows for studying an intact or non-disrupted cell or tissue sample. Such direct tissue analysis allows for fewer artifacts in the sample, thus providing for better accuracy and quantitation of a particular biological molecule.

A "matrix" or a "matrix liquid" refers to a material used in MALDI-MS to prepare the sample analyte for analysis. As noted above, this material absorbs energy from the laser and transfers the energy to the analyte to desorb, volatize, and ionize the analyte, thereby producing ions from the analyte that are then analyzed in the mass spectrometer to yield information about the analyte. Samples of such matrix materials or matrix liquids include, but are not limited to sinapinic acid (SA) and derivatives thereof, such as alpha-cyano sinapinic acid; cinnamic acid and derivatives thereof, such as α-4-cyano hydroxyl cinnamic acid (CHCA); 3,5-dimethoxy-4-hydroxycinnamic acid; 2,5-dihydroxybenzoic acid (DHB); and dithranol. Other examples include heavy metals and glycerol.

The term "polypeptide," "peptide," "oligopeptide," or "protein" as used herein refers to any composition that includes two or more amino acids joined together by a peptide bond. It may be appreciated that polypeptides can contain amino acids other than the 20 amino acids commonly referred to as the 20 naturally occurring amino acids. Also, polypeptides can include one or more amino acids, including the terminal amino acids, which are modified by any means known in the art (whether naturally or non-naturally). Examples of polypeptide modifications include e.g., by glycosylation, or other-post-translational modification. Modifications which may be present in polypeptides of the present invention, include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. For purposes herein, polypeptides include, e.g., proteins, peptides, and/or protein fragments.

Fragment ion spectra are generated by a process called "collision-induced dissociation" or "CID" in which the amide bonds of a peptide are broken, followed by recording of the fragment ion spectrum. Cleavage of amide bonds results in b-ions (containing the N-terminal) and y-ions (containing the C-terminal). High quality MS/MS spectra of tryptic peptides typically show prominent b and y-ion series. If only these two ions were produced for every amide bond in a 10 residue peptide, the fragment ion spectrum would contain 18 peaks. Ideally, long stable ion series of predominately either the b or y-type would be recovered. In reality, peptide fragmentation is variable and moiety dependent, which leads to gaps and difficulties in analysis. Determining the identity and sequence of a peptide from its MS/MS spectrum is complicated both by the variety and variability of the fragment ions produced. Factors that complicate interpretation of MS/MS spectra are missing ion subsets, internal rearrangements, subsequent fragmentations, and multiple charge states. Also to be considered are the relationship of fragment ion peak intensity to ion series origin and fragment masses, influence of amino acid residues and their derivatives, on neighboring amide bond cleavages, and the link between amino acid composition and neutral loss fragmentation.

"Analyzing the protein content" as defined in the present invention refers to the determination of the type or amount of protein in a tissue, cellular or bodily fluid sample using the methods of the present invention.

"Collecting" refers to any means or device for acquiring a sample of tissue, cells or other bodily fluid for analysis by the methods of the present invention.

"Enzymes capable of dissociating" or "enzymes capable of digesting" a tissue sample or cellular or bodily fluid sample are used interchangeably and refer to any one or more enzymes capable of dissociating the individual cells from the connecting extracellular matrix of a tissue or dissociating the individual cells from a cellular mass or bodily fluid. Dissociation can be obtained using any known procedure, including treatment with enzymes such as trypsin, collagenase, lipase and the like.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide. As used herein, the term "fragment" when used in reference to a polypeptide or parent polypeptide is intended to mean any truncated or smaller mass form, corresponding to either carboxyl-terminal, amino-terminal, or both regions, of a reference polypeptide or parent polypeptide. Accordingly, a deletion of a single amino acid from the carboxyl- or amino-terminus is considered a fragment of a parent polypeptide. The term fragment therefore includes deletion of amino acids at the amino- and/or carboxyl-terminus as well as modifications where, for example, an amino acid side chain is removed but the peptide bond remains. A fragment includes a truncated polypeptide that is generated, for example, by polypeptide cleavage using a chemical reagent, enzyme, or energy input. A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid. A fragment can also be generated by a mass spectrometry method including, for example, all types of fragmentation methods and collision induced dissociation (CID). Furthermore, a fragment can also result from multiple cleavage events such that a truncated polypeptide resulting from one cleavage event can be further truncated by additional cleavage events.

A "Signature Map" is defined as a multidimensional representation of a protein alone or as a member of a complex tissue or cellular sample. The signature map includes all the physiochemical properties associated with the intact protein as well as that of the identified and qualified polypeptides thereof. Such physiochemical properties include but are not limited to: Intact protein molecular weight, sub-cellular location, protein class, polypeptide molecular weight, net-charge, post-translational modification. In addition a composite of all assigned signature maps could be interpreted as a global representation of the functional forms of proteins in the tissue or cellular sample. A signature map is often represented as a spectral peak of mass spectrometry data.

"Time and temperature sufficient to obtain dissociated tissue and peptide fragments" as used herein refers to the amount of time and temperature needed for an enzymatic breakdown of a tissue sample that allows for release of cells from the sample and subsequent enzymatic breakdown of cellular proteins into peptide fragments. A person skilled in the art would be cognizant of how to determine the time and temperature sufficient to obtain such dissociation of tissue into peptide fragments. For example, the conditions necessary for optimization of particular enzyme activity is available from the manufacturers of the particular enzymes. In the manner of the present invention the optimal time for digestion of tissue samples using, for example, trypsin, is about 10 minutes to about 2 hours, and in certain situations, for example, the type of tissue or enzyme and the temperature of incubation, longer times are required, perhaps about 24 hours. The optimal temperature for digestion is about 20° C. to about 60° C.

"Tumor tissue" refers to any tissue that harbors cancerous cells. The tumor tissue may be a solid tumor or a non-solid tumor, such as those present in the circulatory system, for example, a leukemia.

"Ischemic tissue" refers to tissue that has been deprived of oxygen due to a decrease in the blood supply to a bodily organ, tissue, or cells caused by constriction, obstruction of, or damage to the blood vessels.

"Data file" refers to the compilation of data from the inventors' internal studies following assessment of various tissue levels of particular biological molecules. After incorporating all of the data acquired following various analyses from different types of cells or tissues, both normal and diseased or abnormal, the data files are now compared to a series of biomolecules identified in an external "database of proteins", for example, the NCBI database.

"Tumor cell extravasation" refers to the process whereby a cancer cell exits a blood vessel or lymphatic vessel.

"Body fluid" refers to any non-solid sample obtained from a subject or patient, for example, blood, serum, plasma, urine, cerebrospinal fluid, amniotic fluid, tears and the like.

"Responders" as used herein refers to a subject or patient who demonstrates a positive outcome from a particular treatment regimen or therapy.

"Non-responders" as used herein refers to a subject or patient who does not demonstrate a positive outcome from a particular treatment regimen or therapy.

"Subject" or "patient" refers to a mammal, preferably a human, in need of treatment for a condition, disorder or disease.

"Post Source Decay" refers to a technique specific to reflectron time-of-flight mass spectrometers where product ions of metastable transitions or collision-induced dissociations generated in the drift tube prior to entering the reflectron are m/z separated to yield product ion spectra.

The term "in situ" as used herein refers to the examination of cells or tissues directly.

The phrase "maintaining biological molecule integrity" or "maintaining protein integrity" are used interchangeably and both refer to the use of solutions that either prevent cross-linking of proteins or prevent tissue autolysis. Alternatively, in order to maintain biological molecule integrity or protein integrity, it is important to avoid the use of known denaturants such as, but not limited to, formalin, formaldehyde, or glutaraldehyde. The use of buffered alcohols is an acceptable means for maintaining biological molecule or protein integrity. Another means of maintaining biological molecule integrity is through the use of a cryoprotectant. A "cryoprotectant" is a compound that prevents cell damage during freezing and thawing processes. Cryoprotectants are agents with high water solubility and low toxicity. Examples of cryoprotectant agents are glycerol, DMSO, sugars, dextran, ethylene glycol, methylene glycol, polyvinyl pyrolidone and hydroxyethyl starch.

The terms "biological molecule" or "biological molecules" or "biomolecules" refer to any one or more of the following constituents of cells or tissues: proteins, polypeptides, or peptide fragments thereof, nucleic acids, including DNA or RNA or an oligonucleotide or fragment or a complement thereof, carbohydrates, lipids, lipoproteins and the like. A biological molecule may also refer to a metabolite, such as, but not limited to, small molecule metabolites, such as sugars, folic acid, uric acid, lactic acid, or glutathione.

"Chemicals capable of dissociating" a tissue sample or cellular or bodily fluid sample refers to any one or more chemicals capable of dissociating the individual cells from the connecting extracellular matrix of a tissue or dissociating the individual cells from a cellular mass or bodily fluid. Examples of such chemicals include cyanogens bromide or formic acid.

A "mechanical means of dissociating" a tissue sample or cellular or bodily fluid sample refers to the use of any one or more mechanical means capable of dissociating the individual cells from the connecting extracellular matrix of a tissue or dissociating the individual cells from a cellular mass or bodily fluid. Examples of such mechanical means include the use of ultrasound, for example, sonication, or the use of a tissue homogenizer or grinder and a sieving mechanism to separate out the individual cellular components from a tissue or bodily fluid.

The term "extracting" or "extraction" refers to the use of a biological, chemical, physical or mechanical means of isolating a biological molecule before analysis by any of the MALDI procedures described herein. Certain methods of extracting are much harsher than others, and these generally include, but are not limited to, procedures such as sonication or homogenization. Moreover, the use of such mechanical means for the isolation of a biological molecule of interest may lead to disruption in the cell or tissue architecture with the production of artifacts. The methods of the present invention avoid the use of such extraction procedures in order to reduce the possibility of introducing such artifacts into the samples under analysis. Another means of extracting a biological molecule is through use of a freezing procedure. However, if one attempts extracting by freezing, it is important to maintain the biological molecule integrity by the prior addition of a cryoprotective agent, such as those used cryoprotectives used in the present invention. Freezing without cryoprotection also leads to disruption of the cellular or tissue architecture and the production of artifacts. Such cryoprotective agents include buffered and non-buffered alcohols, sucrose and other agents such as methylene glycol and General Description In its broadest aspect, the present invention provides a method to characterize, identify and quantify biological molecules in a mixture. The method of the present invention utilizes direct tissue mass spectrometry for characterization of the accurate mass of a plurality of biological molecules in a mixture, particularly wherein a majority of said biological molecules is characterized, such that a majority of the mixture's components may be identified and/or quantitated.

All prior methods of tissue protein analysis required extraction of the proteins from various homogenized or otherwise prepared specimens. As noted above, this allows for the generation of many artifacts within the sample and has other practical problems associated with it. The method described herein provides for direct tissue analysis of biological molecules, such as proteins, by a unique method of preparation and examination of the tissue that will allow direct, rapid, simultaneous analysis of a wide variety and large number of diverse biological molecules, including proteins from normal or abnormal tissues or cells. This method circumvents the need for specialized reagents, such as antibodies, that are dependent on specialized portions of the molecules such as epitopes. This method will thereby characterize the au natural protein composition of cells, fluids and tissues for the purpose of identification of a biomolecule, such as a protein, that could serve as a biomarker for particular diseases or conditions. For example, the use of the methods of the invention for the identification of a particular biomolecule in a diseased tissue or cell sample, which is absent in a sample of normal or non-diseased tissue or cells, would qualify the biomolecule as a biomarker for that disease or condition, such as a cancerous condition. The methods described herein reveal the state of the proteins in their natural environment. This invention, in conjunction with special techniques, such as protein crystallography and electron microscopy, reveals complex molecular structures and configurations (folding, misfolding, and fusion proteins). The present invention reveals changes in protein expression that will allow evaluation of the clinical risk of disease, effect of environmental agents, progress of differentiation and disease or other clinical pathologic conditions. This method is not dependent on the formation of derivatives or other surrogates to identify molecular structure. The method identifies molecular structure from tissues by their molecular mass. The method is independent of studies of genes, DNA, or RNA. Thus, it may disclose entirely new proteins, structures, metabolism and processes. It is applicable to all species of flora and fauna. It is especially useful for clinical purposes to evaluate small amounts of specimens immediately. The method may be practiced under ambient conditions without risk to patients or operators. The method will identify concordant and variant proteins that may appear in sputum, serum, and urine to provide confirmation of risk factors, treatment parameters and protein biomarkers in human disease.

This technique will allow direct tissue and cell analysis of proteins and identify tumors from specimens in the operating room or from biopsy specimens. It will allow human or veterinary surgeons to correctly identify the margins of tumors, and thereby, significantly improve diagnosis, risk evaluation, screening, and therapy of human disease. It will allow analysis of tissues and cells from patients with a variety of pathologic processes using very small specimen samples.

The immediate applications of this invention are in the diagnosis and treatment of disease, including specimens for tumor margins, and the identification of pathologic processes from needle biopsies or other human or experimental animal specimens.

In one embodiment, tissue and biological fluids from biopsies or surgical specimens from human beings or experimental animals are prepared by instantly immersing the specimens in iso-butane cooled by liquid nitrogen. The specimens are then embedded in agar 4% solution which has been boiled and cooled to room temperature. The embedded specimen is cut on a cryo microtome. Forty micron sections are obtained and applied to conductive metal or glass slides. A 0.1% trypsin solution in a buffer, for example, ammonium chloride buffer, or other appropriate digestive enzyme is applied with a micro printer (50μ drops) to the area of interest on the tissue. This is allowed to dry at room temperature, and hydroxy cinnamic acid or other appropriate matrix is applied with a micro printer (50μ drops) on top of the dried trypsin (or other digestive enzyme) on the tissue. The slides are placed in a Maldi Mass spectrometry apparatus (MS/MS) and subjected to a laser beam, and Mass spectrometry time of flight analysis. Protein mass charge (mz) curves are obtained. The predominant species are identified and subjected to further MS analysis and sequencing of the identified peptides. Sequences identified are matched with the known genome databases and the proteins identified.

The method measures the mass of enzymatically, or chemically derived polypeptides in situ without the need for further protein extraction and uses this mass of the polypeptide to assign the peptide fragment to a known protein. This method is used to create detailed ion maps of proteins in the tissue or cellular sample. These ion maps will simultaneously yield accurate identification of and quantitative information regarding proteins in the tissue or cellular sample.

The mass of enzymatically or chemically derived polypeptides is preferably measured or determined to an accuracy of 10 attamols, most preferably to an accuracy of 5 attamols, and particularly preferred to an accuracy of 1 attamol.

Included in the ion maps is information regarding certain physiochemical properties of these enzymatically or chemically derived polypeptides including, but not limited to, the accurate mass and net charge.

The incorporation of an internal standard provides a means for quantitating the abundance of a protein or peptide, thereby accomplishing absolute quantitation of a protein or peptide in a sample. Relative quantitation of protein abundances in complex mixtures is accomplished by comparing ion maps generated in different conditions (i.e diseased vs. non-diseased, treated vs. non-treated).

Thus, an overall method for identifying and quantitating the proteins and/or peptides in a mixture, particularly a complex mixture is provided, whereby a series of experimentally derived highly accurate molecular masses is correlated and compared with a database consisting of theoretical molecular masses.

Proteins in a sample mixture being analyzed may be subject to enzymatic or chemical treatment with the specific intent of generating sub-sequences of polypeptides from such. The resulting polypeptides generated from each subset are then subjected to mass spectrometric analysis, with said methodologies either directly or indirectly coupled to a mass spectrometer. More specifically with respect to electrospray ionization mass spectrometry the elution path of the polypeptides or fragments thereof can be directly coupled to the ionization source of the mass spectrometer. With respect to nano-electrospray ionization mass spectrometry the elution of the polypeptides or fragments thereof can be directly deposited into the nano-electrospray emitter or any connection in fluid registration thereof. With respect to MALDI mass spectrometry the elution of the polypeptides or fragments thereof is directly deposited using time slices or some type of sub-sequence selection methodology, including such methodologies as UV or fluorescence, or electron beam or X-ray to name only a few, onto the MALDI targets. In all instances the ultimate outcome will be generation of a plurality of experimentally derived mass-charge values whose elution/detection time is based on the constraints for elution dictated by the mass or size of the polypeptides or fragments thereof generated by the digestion procedure used prior to polypeptide ionization. A peak picking algorithm, such as Mascot Distiller software by Matrix Sciences, reconstructs a calculated molecular mass map of each subset of enzymatically or chemically treated protein or protein pool, included in which is a listing of all pertinent information relating to the creation of said subset. More specifically included will be the molecular weight range of the intact protein(s), and the intact protein(s) net charge, prior to ionization.

Further, a control or controls of known concentration may be included and placed directly into the selected buffers prior to polypeptide ionization. Preferably, the control will be approximately equimolar. The addition of the control(s) in a known concentration will facilitate quantitation of the identified proteins.

Identifications are made utilizing any of a number of different non-redundant protein or nucleotide sequence databases. These databases are used to predict highly accurate molecular mass maps of any of a number of different enzymatically or chemically digested proteins for comparison with the experimentally derived data. In one embodiment, proteins having a statistically relevant number of peptides whose calculated molecular masses are substantially equal to that of the method's prediction are identified as candidate proteins. For each candidate protein, a plurality of peptide molecular masses are identified based on their accuracy to the method's prediction resulting in a ranked predicted protein list. The peptides identified in the ranked protein list are then cross correlated by their closeness of fit to the characterized properties of the peptide. In one embodiment, a multi-step reiterative process of analysis is provided, wherein mass accuracy is assessed as a first analysis, followed by assessment of correlation by various determined physiochemical properties, including net charge, and protein net charge or size depending on how the sample mixture was characterized.

Additionally by characterization of mixtures under different conditions or from different sources, the method will provide for determining protein concentration, up and/or down regulation, complex formation, post-translational modification, and processing to name only a few, from nonequimolar heterogeneous complex protein mixtures. The skilled artisan may then utilize the resulting information to determine and/or identify therapeutically or diagnostically relevant targets for study, screening, or intervention.

In a particular embodiment, the present invention relates to and demonstrates a method for direct in situ identification of proteins from intact cells and tissues using direct tissue (DT) MALDI TOF analysis, in particular, MALDI-PSD (post source decay) and MALDI-CID (collision induced dissociation). MALDI-PSD identifies peptide spectra from precursor peptide fragmentation ions. These ions are formed by laser fragmentation of the precursor ion, are fully accelerated with the precursor ion, and exit the source, hence the term "post-source decay". MALDI-CID identifies the amino acid sequences of precursor peptide ions isolated in a chamber and fragmented with a high pressure inert gas.

The peptides studied by MALDI-PSD and MALDI-CID are formed, for example, by tryptic digestion of intact proteins. Proteins are identified by insertion of the PSD and/or CID spectral data into the Mascot© ion software for interrogation of the National Bioinformatics (NCBI) database.

The studies presented herein tested whether direct intracellular MALDI-PSD and CID identification of proteins was feasible by establishing tissue and cell preparation methods and applied them to cultured T47D human breast cancer cells, (Olubunmi, et al. *Oncogene* 2002, 21, 7850-7860) and murine stroke model brain tissue slices. (Pevsner, et al. *Toronto*, In press March 2006; Eichenbaum, et al., *J. Pharmacol. & Toxicol Methods* 2002., 47, 67-71; Eichenbaum, et al., *Biotechniques*, 39, 487-488).

The present studies demonstrated successful direct, in situ, identification of Histone H2A.2 in breast cancer cells in culture, and tubulin β2 chain from stroke lesion in the brain. Thus, the demonstration of specific proteins in these preparations established proof of principle that direct tissue MALDI (DT-MALDI) can be used to identify localized changes in type and amount of gene expression for protein directly from cells and tissue without protein extraction. Furthermore, the methods described may be used in a clinical setting to identify diseased or abnormal tissue in a more efficient and expeditious manner.

This feasibility study of DT-MALDI for protein identification from m/z spectra utilized cultured human breast cancer cells and tissue sections from murine brain stroke from photosensitive dye-induced focal ischemic lesions. Following micro application of porcine trypsin on isolated breast cells or tissue slices, the sections were treated with MALDI matrix, 4 cyano hydroxy-cinnamic acid. After first determining a signature map for the tissue with DT-MALDI, m/z spectra of protein/peptide signatures were used to localize and then identify specific signature peaks using MALDI in post-source decay mode and direct MALDI TOF TOF, producing protein fractionation and recording of peptide m/z spectra.

The precise peptide m/z peak values were then analyzed for identification of the respective protein sources using Mascot© (Matrix Science Inc., Boston, Mass.), and Blast© (Blast Internet Services, Pittsboro, N.C.) software to interrogate the NCBI protein database and provide protein match and probability values. From the peptides of fractionated proteins, we were able to clearly identify histone H2A.2 in breast cancer cells, tubulin β2 chain in brain lesions, and myelin basic protein from spinal cord lesions all with high probability scores, and p values of <0.05 or lower. These results are presented as proof of principle for direct identification of proteins from cells and tissues without protein extraction. The relatively small amount of time and effort required for identification of proteins in cultured cells and tissue samples using our direct cytological imaging Maldi approach shows promise of a method to rapidly analyze protein changes in normal, diseased and experimental conditions. Additional refinements in DT Maldi techniques are certain to broaden application to include clinical testing.

Samples for Analysis

Sample Collection

The methods of the present invention, eg. direct tissue MALDI-TOF methods, may be used to identify proteins in complex mixtures and/or to compare quantitatively the relative expression level of proteins between two experimental conditions or within the same experiment.

In one embodiment, the method involves obtaining sample(s) from a subject. Preferably the subject is a human, although collecting samples from non-human subjects is also contemplated. Such non-human subjects include non-human primates. Other non-human subjects include domestic and non-domestic animals, including horses, cows, pigs, sheep, goats, dogs, cats, and rodents, such as but not limited to mice and rats. Such samples can be in liquid or non-liquid form.

Examples of liquid samples that can be obtained from a subject, such as a patient, include, but are not limited to, serum, plasma, whole blood, nipple aspirate, ductal lavage, vaginal fluid, nasal fluid, ear fluid, gastric fluid, pancreatic fluid, trabecular fluid, lung lavage, urine, cerebrospinal fluid, amniotic fluid, saliva, sweat, semen, prostatic fluid, and tears. Examples of non-liquid samples include samples from tissue, bone, hair, cartilage, tumor cells, etc.

Samples may be obtained from a subject suspected of having a particular disease or tissue abnormality. Alternatively, samples may be obtained from individuals whose tissue may be altered as a result of exposure to a drug treatment, genetic manipulations or mutations, injury, change in diet, or aging. In a preferred embodiment, the tissue is altered due to the presence of a disease state. Such disease states include, for example, cancer, cardiovascular disease, inflammatory disease, autoimmune disease, neurological disease, infectious disease and pregnancy or pregnancy related disorders. Control samples are obtained from individuals who do not exhibit the disease state (e.g., an individual who is not affected by a disease or who does not experience negative side effects in response to a given drug).

Subjects suspected of having cancer or a hyperproliferative disorder are studied in some aspects of the invention. Examples of cancers include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, Ewing's sarcoma, reticulum cell sarcoma, myeloma, giant cell tumor, small-cell lung tumor, non-small cell lung carcinoma gallstones, islet cell tumor, primary brain tumor, acute and chronic lymphocytic and granulocytic tumors, hairy-cell tumor, adenoma, hyperplasia, medullary carcinoma, pheochromocytoma, hyperplastic corneal nerve tumor, Wilm's tumor, seminoma, ovarian tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

Cardiovascular disease may be studied in other applications of the invention. Examples of cardiovascular disease include, but are not limited to, congestive heart failure, high blood pressure, arrhythmias, atherosclerosis, cholesterol, long QT syndrome, angina pectoris, tachycardia, bradycardia, atrial fibrillation, ventricular fibrillation, myocardial ischemia, myocardial infarction, cardiac tamponade, myocarditis, pericarditis, heart valve diseases, endocarditis, and aortic valve stenosis.

Inflammatory diseases and autoimmune diseases may be studied in other aspects of the invention. Examples of inflammatory diseases and autoimmune diseases include, but are not limited to, rheumatoid arthritis, non-specific arthritis, inflammatory bowel disease, including but not limited to Crohn's disease and ulcerative colitis, psoriasis, hypothyroidism (e.g., Hashimoto thyroidism), Type 1 diabetes, pelvic inflammatory disease, inflammatory disease of the central nervous system, scleroderma, systemic lupus erythematosus.

Infectious diseases may be studied in still further aspects of the invention. Examples of infectious disease include, but are not limited to, AIDS, hepatitis, SARS, tuberculosis, sexually transmitted diseases, leprosy, lyme disease, malaria, measles, meningitis, mononucleosis, whooping cough, yellow fever, tetanus, encephalitis, and other bacterial, viral, fungal or helminthic diseases.

Neurological diseases or disorders, as well as injuries to the nervous system may be studied in still further aspects of the invention. These neurological diseases, disorders, or injuries include, but are not limited to, dementia, Alzheimer's disease, Parkinson's disease, Amyotrophic Lateral Sclerosis (ALS), multiple sclerosis (MS), spinal cord injury, traumatic brain injury and stroke.

Pregnancy related disorders may be studied in another aspect of the invention, and these include pre-eclampsia, eclampsia pre-term birth, growth restriction in utero, rhesus incompartability, retained placenta, septicemia, separation of the placenta, ectopic pregnancy, hyperemesis gravidarum, placenta previa, erythroblastosis fetalis, pruritic urticarial papulae and plaques.

In some instances, samples may be collected from individuals over a longitudinal period of time (e.g., once a day, once a week, once a month, biannually or annually). The longitudinal period may, for example, also be before, during, and after a drug treatment.

Obtaining numerous samples from an individual over a period of time can be used to verify results from earlier detections and/or to identify an alteration in polypeptide pattern as a result of, for example, drug treatment, pathology, etc. Samples can be obtained from a human subject or a non-human subject. In a preferred embodiment, samples are obtained from humans.

When obtaining a blood, serum, or plasma sample, a coagulation cascade may activate proteases that can induce clotting and cleave proteins in the sample. Preferably, such processes can be prevented or their effect reduced. Thus for serum samples, separating clots from the serum as soon as the clotting process is completed, then freezing the serum as quickly as possible but no longer than within 24 hrs, 12 hrs, 6 hrs, 3 hrs or 1 hr. Similarly for plasma samples, the present invention contemplates removing cells quickly from the blood sample (e.g., in less than 24 hrs, 12 hrs, 6 hrs, 3 hrs, or 1 hr) and the plasma is frozen as soon as possible. Procedures for collection of serum or plasma are known to those skilled in the art.

Methods of Collection of Tissue Samples

The tissue or cellular sample may be collected in any type of collection device that allows for obtaining the sample in the buffer solution necessary to maintain tissue or cellular biological molecule integrity, particularly proteins. Examples include a capillary pipette or tube or slide for tissue analysis after preparing tissue slices using a microtome or ultra cryo microtome. For example, a buffered alcohol solution is a suitable solution for collecting tissue or cellular samples. Formalin, formaldehyde or glutaraldehyde are not recommended, since these solutions allow for protein cross-linking and thus destroy the integrity of the cellular sample or tissue Digestion of the Tissue Sample It is contemplated that the tissue sample to be analyzed by the methods of the present invention must first be digested with enzymes to dissociate the tissue into its cellular components. This may be accomplished using an enzyme, such as, for example, a collagenase or lipase. Alternatively, a chemical means may be used, including chemicals such as formic acid or cyanogen bromide. A second step needed to further digest the sample may include the use of a proteolytic enzyme such as trypsin. However, while the description herein uses a trypsin digestion, other specific digestions are possible, including but not limited to chymotrypsin, endoproteases, Arg C or Lys C, chemical fragmentation methods, such as the cyanogen bromide cleavage, hydroxylamine cleavage, BNPS-Skatole, etc. However, the trypsin (or endoprotease) cleavages are preferred because the resulting polypeptides feature a C-terminal lysine or arginine residue. U.S. Pat. No. 5,821,063 provides digestion methods generally for polypeptides.

Sample Analysis

The utility of both single stage and tandem mass spectrometry for the identification of cellular proteins using protein and nucleotide databases is well documented. In single stage mass spectrometry the instrument of choice has been a Matrix Assisted Laser Desorption Ionization (MALDI) Time of Flight Mass Spectrometer (TOF-MS). The MALDI instrument characteristically generates a mass spectrum of singly charged polypeptide ions with a mass accuracy between 1 attamol to 10 attamols. The generated list of polypeptide ion mass values is then presented to any of a number of previously described search-engines for protein identification (see "Use of mass spectrometric molecular weight information to identify proteins in sequence databases", Biological Mass Spectrometry, June 1993; 22(6): 338-45 by Mann, Hojrup, and Roepstorff, "Identification of 2-D Gel Proteins at the Femtomole Level by Molecular Mass Searching of Peptide Fragments in a Protein Sequence Database" Techniques in Protein Chemistry V, John Crabb editor, 1994, by Henzel, Billeci, Stults, Wong, Grimley and Wantanabe and "Peptide Mass Protein contenting using MALDI-TOF mass spectrometry" (1993) Current Biology 3, 327-332 by Pappin, Hojrup, and Bleasby). Those skilled in this art have coined the name "peptide mass protein contenting" for this method of identifying proteins.

Although peptide mass protein contenting has been shown to facilitate the identification of multiple proteins in simple mixtures (see, Jensen et al., *Analytical Chemistry* Dec. 1, 1997; 69(23): 4741-50), the technique's accuracy fails for complex mixtures increasing the likelihood of generating false positive assignments. Additionally, peptide mass protein contenting cannot be used reliably for quantitative analysis because of ion suppression problems associated with the MALDI ionization process.

An alternative to peptide mass protein contenting is a technique known as tandem mass spectrometry (MS/MS). Tandem mass spectrometric identification of proteins involves introducing a peptide mixture into a tandem mass spectrometer via any of a number of different electrospray ionization techniques. The resulting tandem mass spectrum is interpreted to deduce the amino acid sequence of the polypeptide and the resulting sequence can be compared to a protein or translated nucleotide database for protein identification. Tandem mass spectrometric identifications greatly improve the confidence of MALDI-TOF based protein identifications by providing primary sequence data that confirm the identity generated by the peptide mass protein content. The process of sequence assignment can be tedious and requires a user skilled in the technique of tandem mass spectrometry.

A method eliminating some of the difficulties with the manual interpretation of mass spectrum data discussed above has been described (see Wilm and Mann "Error-tolerant identification of peptides in sequence databases by peptide sequence tags" Analytical Chemistry December 1994; 66(24): 4390-9) earlier. An example of one completely automated process used to identify peptide sequences from raw, uninterpreted tandem mass spectra has been previously described (see U.S. Pat. No. 5,538,897 to Yates and Eng, University of Washington). Though useful in providing a system for rapidly correlating fragment spectra with known protein sequences, the algorithm within these automated processes assigns a most probable match to every spectrum and the user has to rely on multiple unique peptide assignments to the same protein fragment to offset the probability of generating false positives from the peptide MS/MS data. Furthermore, all recent MS/MS based strategies for protein identification involve automatic switching between MS and MS/MS modes of analysis on any polypeptide ion which satisfies user-defined criteria. In an effort to achieve comprehensive protein coverage with nonequimolar heterogeneous mixtures like those seen in typical proteomics applications, the switching occurs often and thereby compromises the quality of both the MS and MS/MS data. Compromising the quality of peptide MS/MS spectra, significantly increases the statistical probability of generating false positive identifications. This is especially true if the number of polypeptide ions from a single protein is low, thereby decreasing the size of the data set for statistical analysis.

To achieve a comprehensive identification of all the components of a given proteome, proposals have been made to combine MALDI-TOF peptide mass protein contenting as a high-throughput first pass analysis followed by a tandem mass spectral approach to identify the proteins missed by the earlier approach. Other approaches suggested by those skilled in proteomics involve generating a very complex peptide mixture by enzymatically digesting all the protein members of a given proteome followed by chromatographic separations interfaced to mass spectrometric techniques such as FTICR (see, "High-Throughput Proteomics Using High-Efficiency Multiple-Capillary Liquid Chromatography with On-Line High-Performance ESI FTICR Mass Spectrometry" by Shen, Y., Tolic, N., Zhao, R., Pasa-Tolic, L., Li, L., Berger, S. J., Harkewicz, R., Anderson, G. A., Belov, M. E., and Smith, R. D., in Anal. Chem. 73 2001) and/or tandem mass spectrometric techniques called MUlti-Dimensional Protein Identification Technology (MUD-PIT, see, "Direct Analysis of Protein Complexes Using Mass Spectrometry" by Link A. J., Eng, J., Scheiltz, D., Carmack, E., Mize, G. J., Morris, D. R., Garvick, B. M., Yates, J. R., III in Nat. Biotechnol. 17, 676-682 1999 and "Large-Scale Analysis of the Yeast Proteome by Multidimensional Protein Identification Technology" by Washburn, M. P., Wolters, D., and Yates, J. R., III in Nat. Biotechnol. 19, 242-247 2001).

Proteomes are generally quite complex. They contain many thousands of proteins, which can range in relative concentration by five or six orders of magnitude. Unlike genomes, proteomes are dynamic. The functional forms of cellular proteins is constantly being modified by post-translational processing and this level of protein expression is affected by many different stimuli. Transcriptional profiling, examining mRNA, is of limited use in deciphering such a dynamic system. Therefore, direct qualitative and quantitative analysis of the actual proteins within the proteome is required to achieve a functional understanding of proteins on a cellular scale. The following section details methods currently used to obtain quantitative protein information. Several biochemical techniques such as staining proteins separated on gels by non-fluorescent dyes (Coomassie Blue, Fast Green), fluorescent dyes (Sypro Red, Sypro Orange), and colloidal metal stains (silver, gold) are used to quantify relative protein amounts. These staining techniques are limited however by poor quantitative precision and accuracy because varying amounts of stain is incorporated into each protein and stained proteins can be difficult to resolve from the background staining of the gel matrix. Other techniques such as introducing radioactive labels, metabolic labeling ($^{14}$C-amino acids, $^{3}$H-leucine, $^{35}$S-methionine) during cellular protein synthesis can overcome some of these problems associated with background noise in the classical staining techniques. Radiolabeling is unfortunately time consuming and expensive and thus not practical on a routine basis. To overcome the shortcomings associated with quantitating proteins using gel-based staining and radiolabeling techniques, researchers have used mass spectral based methods. One such method uses MS-isotopic labeling techniques to perform accurate quantitation of the relative quantities of proteins in cells grown under different conditions. In this procedure, stable isotopes such as $^{15}$N are introduced into the cell growth medium. The $^{15}$N-enriched proteins produced during the cell growth process are then compared with unaltered proteins by mixing the two and analyzing them together. The corresponding $^{15}$N labeled polypeptides are compared with their $^{14}$N companion because they have almost identical physical properties except the predicted mass shift. This strategy makes it possible to record fairly accurately the quantitative differences between native and isotopically enriched "companion" peptides (see Oda, et al., *Proc. Natl. Acad. Sci. USA* 96 6591-6596 1999). However, this strategy has limited utility because it requires treatment with an enriched stable isotope medium prior to protein isolation. Another approach that overcomes this shortcoming was presented recently (see, "Quantitative analysis of complex protein mixtures using isotope-coded affinity tags" by Gygi, et al., *Nat. Biotechnol.*, 17, 994-999, 1999 and "Quantitative proteomic analysis using a MALDI quadrupole time-of-flight mass spectrometer" by Griffin, et al., *Anal. Chem.*, 73, 978-986 2001). This approach involves derivatizing protein mixtures with heavy and light isotope-coded affinity tags (ICAT). These tags are covalently bound to specific amino acid residues. The proteins are then digested and the tagged peptides are affinity purified for subsequent quantitative analysis. The affinity-purified fractions are subjected to sequence identification using tandem mass spectrometry methods and concurrently analyzed to measure the relative expression levels of individual proteins from complex, control and experimental protein mixtures. Early development of this technology suggested that it was fairly robust and could be widely applicable. Even this method is plagued, however, with the poor yields associated with incomplete tagging and the affinity purification steps. Another problem with this approach is that it is only useful for proteins containing at least one free cysteine group. An example of this pitfall is illustrated by the fact that 35% of the yeast ribosomal proteins are cysteine-free and therefore cannot be identified or quantified using the ICAT technology. Furthermore these tagged polypeptides must be of a mass amenable to sensitive MS analysis.

Mass analysis data or spectra may be used with known sequencing algorithms to yield the amino acid sequence of the peptide analyte (Taylor, et al. *Rapid Communications in Mass Spectrometry*, 11, 1067-1075, 1997; Chen, et al., *Journal of Computational Biology*, 8(6), 571-583, 2001; Dancik, et al., *Journal of Computational Biology*, 6, 327-342, 1999; Eng, et al., *J. Am. Soc. Spectrom.*, 5:976-989, 1994; Mann, et al., *Anal. Chem.*, 66:4390-4399, 1994). These algorithms are well known and can be used with some degree of utility regardless of the accuracy or precision of the mass analysis data. The improvement in data acquisition and mass spectra quality provided by the present invention increases the accuracy of each mass measurement and increases the utility of sequencing algorithms, increases the accuracy of the sequence information and the length of the polypeptide sequence that can accurately be determined. The methods of the present invention include applying available sequencing algorithms to the sequence information obtained from mass analysis of polypeptides identified directly in situ without the need for further protein extraction.

In many proteomics studies and basic biological assays, the critical determination is an identification of the identity of an analyte protein, sometimes as present in a biological sample. Typically, proteomics databases operate by aligning an experimentally-determined amino acid sequence against a large number of reference amino acid sequences in a database of full-length proteins and identified protein fragments. As is readily appreciated, an increase in the accuracy of sequence information and in the number of sequences identified in a polypeptide analyte will improve the utility of comparing or identifying experimentally-determined polypeptide fragments against reference sequencing. Accordingly, one aspect of the invention is the use of sequence data obtained from mass analysis of the polypeptides described herein to identify proteins by submitting the amino acid sequence, determined from experimental MS data, to a protein database to identify the analyte and/or to identify the analyte as a component of a sample.

It has been shown that five or more amino acid sequences in series (contiguous sequence with no gaps) can be used to search databases to identify a protein with high confidence (Mann, et al., *Anal. Chem.*, 66:4390-4399, 1994). These lengths of amino acid sequence have been referred to as critical length sequence tags. Longer amino acid sequence tag could dramatically increase identification accuracy, which is very useful, when many proteins in the database share certain amounts of evolutionarily conserved sequences. Longer amino acid sequence tags also increase the confidence of protein identification for organisms without fully or adequately sequenced genomes. However, when a gap is found in a sequence tag, (for example, instead of a five consecutive amino acid tag, there is a three amino acid tag plus a gap of variable length, followed by a two amino acid tag), the protein identification becomes very difficult. More proteins can be matched to the smaller sequence tags, and because the directionality of the two small tags is also unknown, the protein identification is very unreliable. Mann and Wilm have proposed that the minimum sequence tag for 85% confident protein identification should be at least three to four contiguous residues, but clearly longer sequence tags are beneficial.

The methods of the present invention may be used to differentiate between the proteins or polypeptides or fragments thereof in a diseased or abnormal tissue as compared to a normal tissue, that is, where any difference in mass analysis can be attributed to a disease or any physiological condition of clinical interest. For example, where a protein mutation is known to be responsible for a particular disease state, and where the mutation is known and results in a difference in mass from the native polypeptide, or that polypeptide representing a normal or non-disease state, a clinical diagnosis may be made from the mass analysis by comparing the mass of a polypeptide analyte in a patient sample from the known mass in the native or non-disease state. Data processing of the mass data or spectra includes the step of determining the mass of at least one polypeptide fragment comprised of a portion of the patient sample and comparing that result with the known mass for the non-disease state. A comparison of the patient and normal samples indicates whether or not the disease state is present. Because the tissue sample can be analyzed in situ for protein or polypeptide identification without the need for further protein extraction procedures, the present invention enhances the ability to perform de novo protein analysis in a high throughput fashion. In addition, the invention also increases the utility of the DT-MALDI TOF technique for clinical diagnosis and large scale screenings for any detection of polypeptide sequences.

Further MALDI Analytical Methods

Particular embodiments of the present invention may have application in detecting cancer, inflammation, infection, swelling or edema, scar tissue, etc. Also, embodiments of the present invention could be used to define metabolic pathways that are functioning within tissue in an organ system. Particular embodiments of the present invention provide for the detection of diseased or abnormal tissue or injury to a tissue.

MALDI-TOF mass spectrometry (Biflex and Autoflex MALDI-TOF mass spectrometers (Bruker Daltonics) can be used) and SpectroTYPER RT® software (Sequenom, Inc.) can be used to analyze and interpret the SNP genotype for each sample.

A laser desorption time-of-flight mass spectrometer may be used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry, or MALDI-MS, is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry. MALDI-MS is useful for detecting the biological molecules of the invention if the complexity of a sample has been substantially reduced using the preparation methods described above.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI technology is available from Ciphergen Biosystems, Inc., Fremont Calif. as part of the ProteinChip®. System. ProteinChip® arrays are particularly adapted for use in SELDI. SELDI is described, for example, in: U.S. Pat. No. 5,719,060 ("Method and Apparatus for Desorption and Ionization of Analytes, "Hutchens and Yip, Feb. 17, 1998,) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Xenogen provides the VivoVision imaging method, which utilizes in vivo biophotonic imaging, which non-invasively illuminates and monitors biological processes taking place in a living mammal in real time. In this procedure, luciferase is incorporated into cells and animals. Once it is activated, light is emitted and VivoVision captures this image and analyzes it. This procedure may be used to track gene expression, or the spread of disease or the effect of a new drug candidate.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector.

The detector then translates information of the detected ions into mass-to-charge ratios. Detection of the presence of markers or other substances will typically involve detection of signal intensity. This, in turn, can reflect the quantity and character of markers bound to the substrate. Any of the components of a mass spectrometer (e.g., a desorption source, a mass analyzer, a detector, etc.) can be combined with other suitable components described herein or others known in the art in embodiments of the invention.

In another embodiment, an ion mobility spectrometer can be used to detect markers. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in a sample. One advantage of ion mobility spectrometry is that it can operate at atmospheric pressure.

In yet another embodiment, a total ion current measuring device can be used to detect and characterize markers. This device can be used when the substrate has only a single type of marker. When a single type of marker is on the substrate, the total current generated from the ionized marker reflects the quantity and other characteristics of the marker. The total ion current produced by the marker can then be compared to a control (e.g., a total ion current of a known compound). The quantity or other characteristics of the marker can then be determined.

Data generated by desorption and detection of protein markers can be analyzed using any suitable means. In one embodiment, data is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a serum protein) may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., women in whom human cancer is undetectable).

Any suitable method can be used to detect a biological molecule or molecules in a sample. For example, gas phase ion spectrometry can be used and confirmation made by using an immunoassay as known to those skilled in the art, eg. ELISA assays. Using these methods, one or more biological molecules can be detected. Preferably, a sample is tested for the presence of a plurality of biological molecules. Detecting the presence of a plurality of biological molecules, rather than a single biological molecule alone, would provide more information for the diagnostician. Specifically, the detection of a plurality of biological molecules in a sample would increase the percentage of true positive and true negative diagnoses and would decrease the percentage of false positive or false negative diagnoses.

The detection of the biological molecule or biological molecules is then correlated with a probable diagnosis of human disease, such as cancer. In some embodiments, the detection of the mere presence or absence of a biological molecule, without quantifying the amount of biological molecule, is useful and can be correlated with a probable diagnosis of human disease. In other embodiments, the detection of biological molecules can involve quantifying the biological molecules to correlate the detection of biological molecules with a probable diagnosis of human disease. Thus, if the amount of the biological molecules detected in a subject being tested is higher compared to a control amount, then the subject being tested has a higher probability of having a human disease.

Similarly, in another embodiment, the detection of biological molecules can further involve quantifying the biological molecules to correlate the detection of biological molecules with a probable diagnosis of human disease, such as cancer, wherein the biological molecules are present in lower quantities in blood serum samples from human cancer patients than in blood serum samples of normal subjects. Thus, if the amount of the biological molecules detected in a subject being tested is lower compared to a control amount, then the subject being tested has a higher probability of having a human cancer.

When the biological molecules are quantified, they can be compared to a control. A control can be, e.g., the average or median amount of biological molecules present in comparable samples of normal subjects in whom human cancer is undetectable. The control amount is measured under the same or substantially similar experimental conditions as in measuring the test amount. For example, if a test sample is obtained from a subject's blood serum sample and a biological molecule is detected using a particular probe, then a control amount of the biological molecule is preferably determined from a serum sample of a patient using the same probe. It is preferred that the control amount of biological molecule is determined based upon a significant number of samples from normal subjects who do not have human cancer so that it reflects variations of the biological molecule amounts in that population.

Data generated by mass spectrometry can then be analyzed by a computer software. The software can comprise code that converts signal from the mass spectrometer into computer readable form. The software also can include code that applies an algorithm to the analysis of the signal to determine whether the signal represents a "peak" in the signal corresponding to a biological molecule of this invention, or other useful biological molecules. The software also can include code that executes an algorithm that compares signal from a test sample to a typical signal characteristic of "normal" and human cancer and determines the closeness of fit between the two signals. The software also can include code indicating which the test sample is closest to, thereby providing a probable diagnosis.

Buffers

In another embodiment, the solution used to maintain tissue or cellular biological molecule integrity, particularly protein integrity, is a buffered solution. As noted above, the buffer chosen for a particular analytical procedure following the perfusion would be prepared in accordance with the optimal pH of the analyte to be obtained from the tissue, organ or cell system under analysis. One of skill in the art would be cognizant of this fact. In a particular embodiment, the buffer is selected from the group consisting of phosphate buffered saline (PBS), a phosphate buffer, a potassium buffer, a choline buffer and a glycine buffer.

Matrix Liquid

In another embodiment, the tissue or cellular sample is prepared for analysis using a matrix liquid for use in matrix assisted laser desorption ionizing imaging (MALDI) mass spectrometry (MS). Examples of such matrices include α-4-cyano hydroxyl cinnamic acid (CHCA), sinnapinic acid, a heavy metal such as, but not limited to, gadolinium, cobalt and bismuth and glycerol. The choice of matrix depends on the system to be studied. For example, 2,5-dihydroxybenzoic acid (DHB) is often used with peptides, proteins, lipids and oligosaccharides. 3,5-dimethoxy-4-hydroxycinnamic acid is often used with peptides, proteins and glycoproteins. α-cyano-4-hydroxycinnamic acid (CHCA) is often used with peptides, proteins, lipids and oligonucleotides. The matrix may be prepared at a concentration of about 10 mM, although this concentration may be modified depending on the circumstances presented. (See U.S. Pat. Nos. 5,716,825; 5,705,813; 5,854,486; 5,808,300; 6,639,217; 6,677,161; 6,680,477; 6,706,530 and 6,723,564).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Direct MALDI Cellular and Tissue Identification of Proteins Materials and Methods All studies were approved by NYU IRB and IACUC protocols. Chemicals were purchased from: Sigma (St. Louis, Mo., USA), Invitrogen (Carlsbad, Calif., USA), Sakura Finetek (Torrence, Calif., USA), and Scott Specialty Gasses (Plumsteadville, Pa., USA), and used without further purification. All samples were analyzed with an Axima-CFR+ (PSD) or QIT (CID) (Shimadzu, Columbia, Md., USA). The instruments were calibrated with four point samples of CHCA (a-cyano-4-hydroxy-cinnamic acid): 190.04 (M+H)—monoisotopic, bradykinin Fragment 1-7: 757.40 (M+H)—monoisotopic, angiotensin II (human): 1046.54 (M+H)—monoisotopic, cytochrome C (equine): 12,361.96 (M+H)—average, aldolase (rabbit muscle): 39,212.28 (M+H)—average, and albumin (Bovine serum): 66,430.09 (M+H)—average. MALDI-PSD and CID were chosen for this study because we could study both larger proteins and significantly larger peptides.

Cells

Cells—Human breast cancer cells (T47D) grown to 70% confluence in DMEM media (Invitrogen) containing 10% fetal bovine serum, FBS (Invitrogen) in six Petri dishes, approximately 106 cells per dish. The media was aspirated and the cells washed with PBS. The cells from each of the Petri dishes were scraped into Eppendorf tubes. Distilled water, 0.5% polyvinylpyrrolidone (PVP 360) in 60% methanol, 0.5% polyvinylpyrrolidone (PVP 360) in both 60% methanol and 95% ethanol, were added to separate dishes, and 0.5% polyethylene glycol sorbitan monolaurate, Tween 20 in both 60% methanol and 95% ethanol, was added to separate dishes. Cells treated with distilled water were scraped into an Eppendorf tube, and placed on ice for five minutes. After the water was aspirated, the cells were centrifuged at 3000 rpm for five minutes. Cells in one of the Petri dishes treated with PVP 360 in 60% methanol were washed with methanol 60% to remove the PVP 360 and scraped into the Eppendorf tube. All of the other cells from each dish were scraped into separate Eppendorf tubes, centrifuged, and the supernatant removed.

All pellets were allowed to air dry at room temperature. Porcine trypsin (0.2 mM in 25 mM ammonium bicarbonate buffer, pH 8-8.5) was added to each of the six samples for ninety minutes at 37° C. A 1.5 µl aliquot of the trypsin-cell lysate (approximately 105 cells) was spotted onto conductive metal plates wells (Shimadzu, Columbia, Md., USA) and allowed to dry at room temperature Matrix (alpha 4 cyano hydroxy-cinnamic acid) 10 mg/ml 0 in 50:50 acetonitrile 0.1% trifluoroacetic acid in water was robotically printed over the trypsin with a chemical printer and allowed to crystallize at room temperature. This printer co-registers all printed microdots, so that the MALDI laser raster is aimed at precisely the same place where the matrix is applied.

Tissues

Adult Swiss mice were treated by a modification of a protocol for noninvasive photochemically induced murine brain lesions. This method is based on the fluorescent photochemical reaction between Rose Bengal and visible light that releases singlet oxygen molecules. When released in vessels, singlet oxygen causes arterial thrombosis and focal neuronal apoptosis in the brain and spinal cord. This non-invasive model was chosen for operator controlled lesion size and absence of inflammatory change attendant upon larger vascular occlusive or open surgical models of stroke and spinal cord injury. In this model, Rose Bengal was injected intraperitoneally at a dose of 3 mg/kg. After Rose Bengal was injected into the peritoneum, light was applied to the scalp with a cold fibreoptic light pipe over the right parietal cortex. The left parietal cortex received no light exposure, and was the control hemisphere. The light-exposure time was 10 minutes for the brain lesions. Cerebral brain tissue was studied at 24 hours post-noninvasive photochemical stroke (Eichenbaum, et al., *J. Pharmacol. & Toxicol Methods* 2002., 47, 67-71; Pevsner, et al., *Journal Pharmacol. & Toxicol Methods* 2001, 45, 227-233).

The mice were anesthetized (isofluorane 1%, Scott Specialty Gasses, Plumsteadville, Pa.) and infused with 7% sucrose by percutaneous transthoracic left ventricular injection (Eichenbaum, et al., *Biotechniques,* 39, 487-488).

Under terminal anesthesia, the brain was rapidly removed, frozen in isopentane and affixed to the cryo microtome chuck with a few drops of ice water. No embedding media was used since agar, a galactose polysaccharide and Tissue-Tek® O.C.T.™, a mixture of polyvinyl alcohol and polyethylene glycol (Sakura Finetek) interfere with MALDI. Twelve µ cryo-sections were obtained for both histological slides and DT-MALDI, with the tissue temperature adjusted between −5 and −15° C. while the knife temperature was kept at −20° C. This temperature combination gave the best artifact free tissue sections. Mirror sections were applied to standard glass slides for histology and conductive metal plates for DT-MALDI (Shimadzu, Columbia, Md., USA). Both the glass slides and conductive metal plates were immediately immersed in 60% methanol for fixation.

Porcine trypsin (60 k picoliters) was applied to brain slices using a computer networked, chemical printer (Shimadzu Chemical Printer Chip 1000, Columbia, Md., USA), that delivers pico-liter drops via a robotic interface. This printer can co-register multiple printings and link the printer sites on the plates with the Maldi mass spectrometer (Shimadzu Biotech Axima CFR Plus). The printer is fitted with a microscope to allow direct visual confirmation of uniform co-registration of solutions, in this instance trypsin and matrix, for high spatial resolution. Tryptic digestion was continued in an incubator for 90 minutes at 37° C., and the sections dried at room temperature. Matrix was printed on the same trypsin loci and crystallized at room temperature. The location of each microdot of trypsin and matrix solution was forwarded to the networked MALDI TOF mass spectrometer. Matrix (alpha 4 cyano hydroxy-cinnamic acid 10 mg/ml in 50:50 acetonitrile (Sigma): 0.1% Trifluoroacetic acid in water (Sigma) was printed on undigested and digested tissue sections of brain. Matrix was spotted over each trypsin dot, using the same chemical printer. The chemical printer was also used to spot matrix onto the dried trypsin-cell lysate in the wells of the conductive metal plates. The prepared cells and tissues slices were examined with a MALDI-TOF and MALDI-TOF TOF mass spectrometer. The printer is fitted with a microscope to allow direct visual confirmation of uniform co-registration of solutions, in this instance trypsin and matrix, for high spatial resolution.

Twelve cell samples in twelve different 1 mm wells on the conductive plates were covered by a targeted 400 pulse laser raster. A similar raster was used over the previously selected, 1 mm matrix-printed lesioned and control sites in the brain and spinal cord slices. Protein and peptide m/z spectra were generated with MALDI-TOF and MALDI TOF-TOF respectively. The peptide m/z spectra were further analyzed via Mascot© interrogation of the NCBI protein database.

MALDI Sample Analysis and Identification of Observed Proteins

Each laser pulse utilizes light optics to focus the nitrogen laser to approximately a 100 micron beam. The position of the conductive plate is controlled by a preset raster. A targeted 400 pulse laser raster was positioned over each 1 mm diameter sample well or tissue section on the conductive plates. A rectangular raster configuration was used for these experiments. The plate is stepped at 4µ intervals between each laser firing. The co-registration coordinates generated by the chemical printer were used for the robotic movement of the plate in the MALDI-TOF and MALDI-TOF TOF mass spectrometer.

The sampling protocols were as follows:

Cells: There were twelve wells with approximately $10^5$ cells per well, and. Each well was sampled 400 times for a total of 4800 data points.

Figure 2:
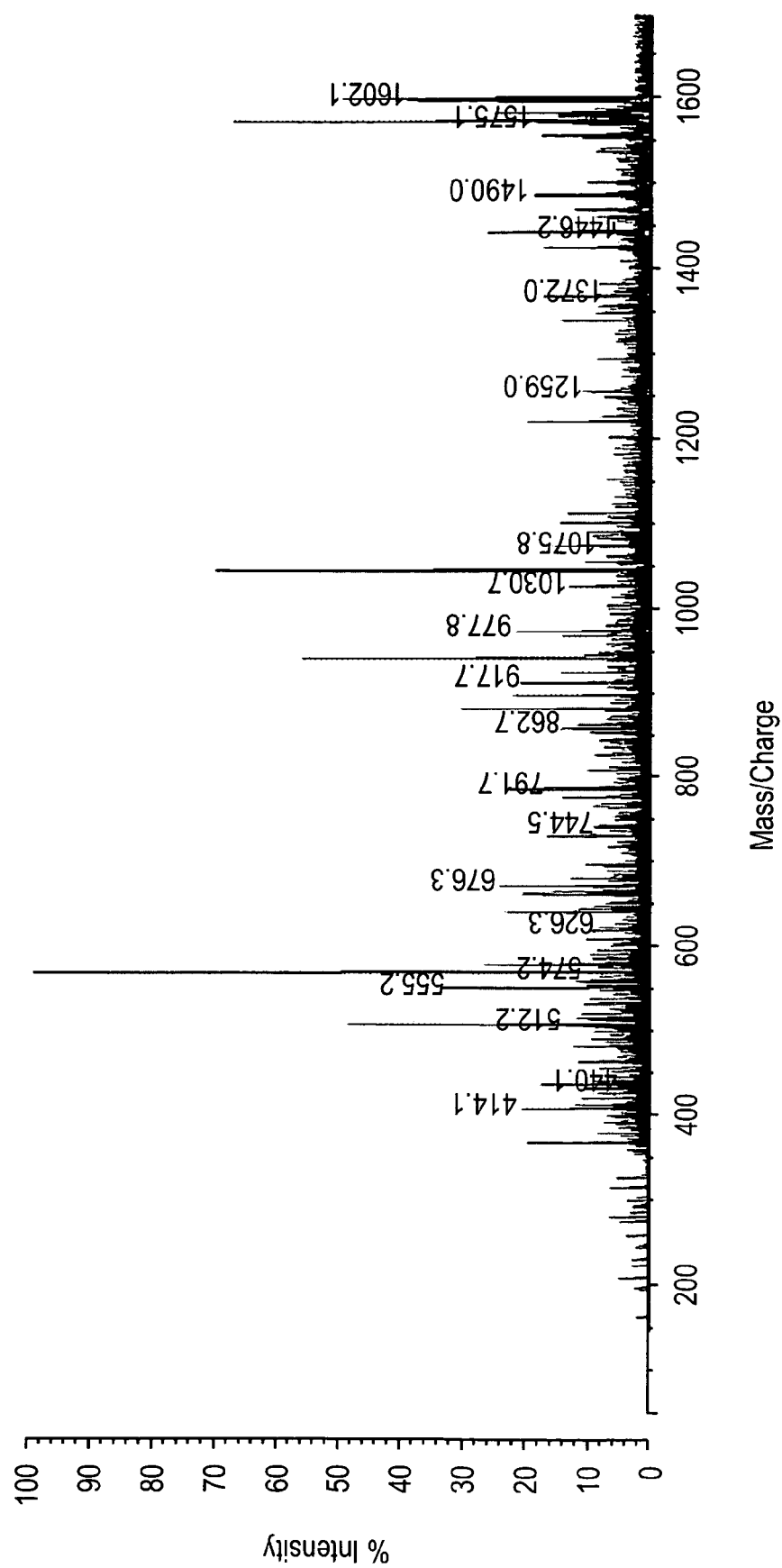
FIG. 2: Stroke model tubulin Mass spectrum of Maldi PSD fragmentation peptides from precursor ion LHFFMPGFAPLTSR, (SEQ. ID. NO. 2) mass 1621.0.

Tissue: Five normal hemisphere brain sites and six lesioned brain sites were sampled on each section of brain from six animals for a total of 12,000 stroke brain data points and 10,000 normal brain data points per brain slice. Each m/z spectrum represents the average of laser pulses from each brain slice. The lesions were virtually identical. Individual peptide fragment mass units obtained from the PSD and CID spectra were inserted into the Mascot© software program to interrogate the NCBI protein database, (FIGS. 1 and 2). Protein identification with probability scores and corresponding (p) values were obtained from this analysis. There are no special chemical hazards or safety considerations. Since this was not a population report, no further statistics were applied.

Results

Application of DT-MALDI to each of our specimen types, cells or tissue, produced complex peptide or protein spectra over a range of 700 to 150,000 Da, similar to those reported from tissue homogenates subjected to MALDI analysis (Hansen, et al., *Molecular & Cellular Proteomics* 2003, 2, 299-314; Luo, et al., *Molecular Biotechnology* 2005, 29, 233-244; Malmstrom, et al., *Proteomics* 2002, 2, 394-404). For the detection of intact high mass proteins the MALDI TOF was operated in linear mode. In this case no digestion was performed; only matrix was "printed" onto the tissue with a chemical printer (Shimadzu Chemical Printer Chip 1000, Columbia, Md., USA). In cases where digestion was performed, trypsin and then matrix were printed in the exact same loci. In this study the most abundant peptides from the trypsin digest were selected for either PSD or CID analysis. Each spectral peak represented a protein locus on the tissue or cell map. Since our goal was to identify proteins from cells and tissues, we chose peptide peaks with the largest amplitude from each specimen group. The corresponding mass number was used for peptide precursor analysis by PSD or CID. This analysis produced MALDI mass charge, m/z spectra, representing an array of peptide fragments from the precursor peptide. The resulting mass/intensity data were loaded into Mascot© ms ms ion search software for determination of the proteins represented by these peptide fragments. Future studies will be conducted using other peaks for complete profile analysis, protein identification, and possible quantification.

Cell Analysis

For cell culture studies we varied the sample preparation by choice of detergents and the use of distilled water. The cells that gave the most abundant profiles indicating the least amount of signal interference were those treated with polyvinylpyrrolidone, PVP 360, detergent in 60% methanol and washed three times with 60% methanol to remove the PVP 360. The next best signal was obtained from cells washed with distilled water alone, which lysed the cellular plasma membrane and exposed the cytoplasm. The cells from PVP 360 in methanol or ethanol, and Tween in methanol or ethanol without further alcohol wash gave the least distinct profiles. In fact, no identifiable peaks were obtained from the Tween-treated samples. The most abundant precursor peptide from the cells treated with PVP 360 measured 1742.8 Da by MALDI-PSD. Analysis with Mascot© query of the National Bioinformatics database (NCBI) revealed a match with the nuclear protein Histone 2H2B, Mascot© score 93, p value <0.001 (2e-07), MW 13,942 Da, Peptide Mass Tolerance: .+−.1.5 Da, Fragment Mass Tolerance: .+−.1.5 Da, Max Missed Cleavages: 1, Spectra, FIG. 1. Detailed Mascot search HTML, See FIGS. 5-12.

Brain Lesion Analysis

Figure 3B:
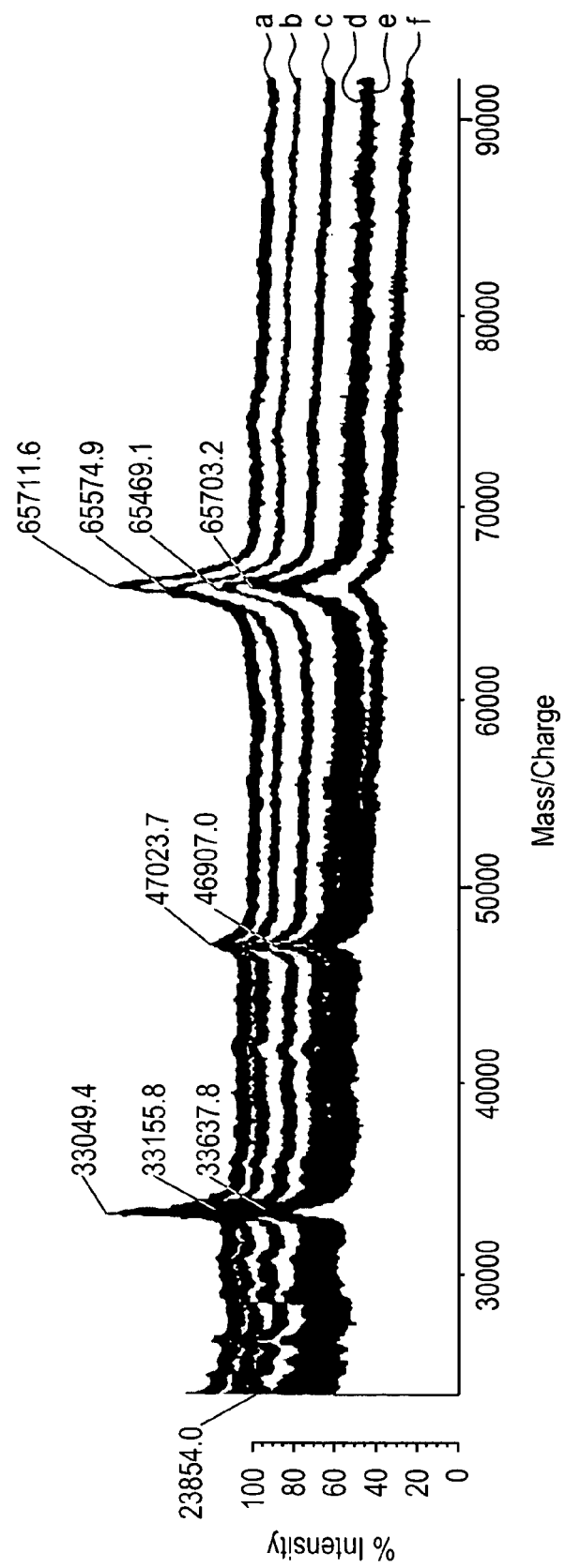
Figure 4:
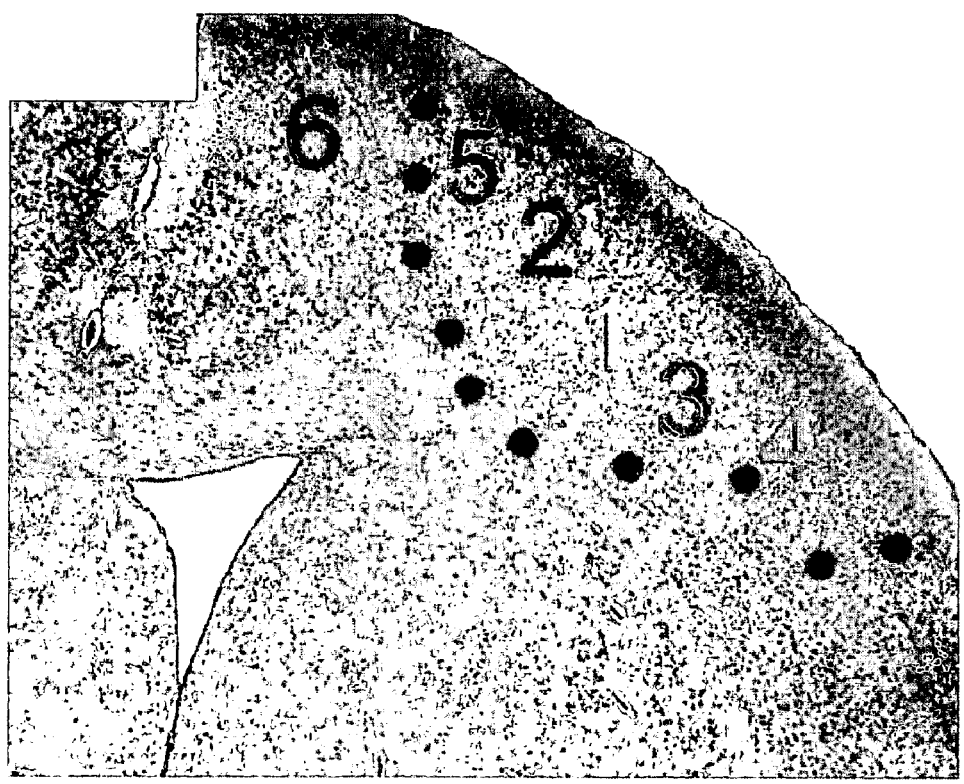
FIG. 4: Histologic photomicrograph of the lesioned hemisphere. Note the edema, hyperchromatic nuclei, and paucity of neurons in the lesion compared to the surrounding normal brain. Maldi TOF sampling loci are marked by colored numbers corresponding to the observed spectra in FIG. 3. These numbers represent decreasing lesion size (1-5), and normal ipsilateral cingulate gyms (6). Note the lesion penumbra (red dots).

Comparison mapping of lesioned and non-lesioned (control) cerebral hemispheres produced differential intensity (peak height) of a 65 kDa protein signature peak (FIG. 3). The height of the 65 kDa peaks was greatest at the center of the histologically confirmed lesion while the peak height tailed-off with distance from the lesion (FIG. 4). The peak height was least at the normal ipsilateral cingulate gyrus and remained at this level through the entire un-lesioned hemisphere. Thus, there was a direct quantitative correlation between the histology and m/z spectral peaks. Two other protein peaks at 33 kDa and 43 kDa had virtually the same intensities in both hemispheres (FIG. 3). In this study the predominant MALDI-CID measured peptide in the lesioned hemisphere had a mass of 1621.0 Da. Mascot© analysis of this peptide spectra yielded a match for tubulin β2 chain, Mascot© score of 47 and p value <0.05, MW 49,875, Peptide Mass Tolerance: ±0.5 Da, Fragment Mass Tolerance: ±0.8 Da, and Max Missed Cleavages: 1, Spectra, (FIG. 2). Detailed Mascot search HTML, FIGS. 13-18.

Discussion

The goal of this study was to determine the feasibility of DT-MALDI for in situ identification of proteins directly from trypsinized tissue by a unique application of matrix directly over complex cells and tissues. MALDI requires matrix crystals that vaporize peptide and protein molecules into a charged field within a vacuum chamber. The matrix particle size, shape, light scattering properties and charge all have an effect on the transfer of the laser light energy sufficient to produce ionization of the analyte. 1, 16-19 The ideal matrix has low heat capacity that is critical for generating intact gas-phase ions of the analyte molecule while minimizing decomposition of the analyte. It must also have effective absorbance across a wide range of wavelengths to promote rapid ionization of the analyte for immediate transfer of the laser energy. Only a small number of low mass peaks should be generated from the matrix alone, so as not to interfere with low molecular weight mass determinations of compounds such as amino acids, steroids, sugars surfactants and polymers. The compounds 2,5-dihydroxybenzoic acid (DHBA), hydroxy cinnamic acid and sinnapinic acid all produce complicated spectra at or just below 500 Da, but none of these spectra are associated with the analyte. They are widely used because they appear to produce higher spectral signal from larger peptide fragments. The matrix chosen for this study was 4 cyano hydroxy cinnamic acid because of its known efficacy in the identification of medium-sized, 1000 to 5000 Da peptides. Co-UFP produces no signal above 100 Da, and may have some distinct advantages for use with low mass compounds. In addition, new synthetic laser energy-absorbing polymers that effectively eliminate the matrix addition step and the use of requisite small organic chemical matrices from MALDI are under study. The resulting polyelectrolyte-assisted laser desorption/ionization method has been proven to have some exceptional advantages over current MALDI methods. First, the matrix addition step can be eliminated. Second, the low molecular weight signal from energy-absorbing matrix molecules is minimized by covalently linking the energy-absorbing molecules to the backbone of the polymer and other ionization-enhancing pendant groups on the backbone. The elimination of these low molecular weight matrix by products will enhance our ability to identify small signaling molecules or drugs with DT-MALDI (Kitagawa, *Analytical Chemistry* 2006, 78, 459-469).

Recent studies suggest that we can achieve MALDI resolution in the range of 25 mµ, with matrix ablation techniques and appropriate sampling with the existing lasers that are 50 microns or larger in diameter. This should allow resolution of many low level proteins in cell and tissue samples (Crossman, et al., *Rapid Communications in Mass Spectrometry* 2006, 20, 284-290; Jurchen, et al., *Journal of the American Society for Mass Spectrometry* 2005, 16, 1654-1659).

Specimen preparation was shown to have a profound effect on protein identification from dissociated cell cultures and tissue slice specimens. Cells and tissue samples must be obtained fresh, frozen immediately, and fixed with alcohol. Alcohol does not cross-link proteins and escapes the preparation at the time of vaporization. Methyl and ethyl alcohol were equally effective agents for cells and tissue. Protein cross-linking agents, formalin or glutaraldehyde, produced insufficient MALDI signal in our material for protein identification. However, the successful use of p-nitroaniline, as an alternate matrix in formalin fixed tissue, was recently reported (Rujoi, et al., *Anal Chem* 2004, 76, 1657-1663).

Tissue sections must be as thin as possible. Thin sections, 12 microns or less are necessary to avoid differential extraction efficiency of matrix solvent in different tissues since MALDI is a surface phenomenon. We and others have found thinner slices always produced higher Mascot© scores (Crossman, et al., *Rapid Communications in Mass Spectrometry* 2006, 20, 284-290).

Digestion of proteins is critical to obtain peptide fragments. Dimethylated porcine proteomics grade trypsin purified through affinity chromatography and lyophilization was chosen for its highly specific cleavage of peptide bonds at the carboxyl side of arginyl and lysil residues. Trypsin digestion is both time and temperature dependent. Even though ninety minutes at 37° was adequate in this study, we have successfully used variations of time and temperature to obtain peptide fragments. In a recent report, tryptic digestion in 80% acetonitrile yielded over 52% more peptides than the overnight digestion of 1 ug of a protein mixture in purely aqueous buffer (Strader, et al., *Analytical Chemistry* 2006, 78, 125-134). The use of acetonitrile should enhance the yield of low level protein identification. Microwave treatment of spores combined with formic acid has been recently described to amplify the digestive effects of formic acid and identify spore specific proteins (Swatkoski, et al., *Anal Chem* 2006, 78, 181-188). While trypsin is a well-known and accepted protease, there are additional enzymes that may have advantages or be complementary to trypsin (Schechter, *Current Protein & Peptide Science* 2005, 6, 501-512). Proteinase K (Sigma) has been used successfully to prepare extractions for MALDI RNA determination from formalin fixed liver (Masuda, et al., *Nucl. Acids Res.* 1999, 27, 4436-4443). The spectra obtained with this technique may be useful on our alcohol-fixed cells and tissues.

The choice of detergent and its removal with alcohol can materially affect the m/z spectra obtained from both undigested and digested samples. Non-diagnostic m/z spectra were obtained from the cell samples treated with PVP 360 in methanol or ethyl alcohol that were not washed with alcohol to remove the detergent.

Review of the literature reveals a lack of agreement regarding detergents and their use. This mirrors our experience. The addition of a variety of detergents in the starting solution including ionic SDS, non-ionic Triton X-100 and n-octyl beta-D-glucopyranoside, and zwitterionic CHAPS, 3-[(3-cholamidopropyl)dimethylammonio]-1-propanesulfonate, have been by others to achieve maximum solubilization of membrane proteins increasing the yield from 178 to 268 membrane proteins with minimal interference with LC-MS/MS analysis (Lu, et al., *Molecular & Cellular Proteomics* 2005, 4, 1948-1958). Cleavable detergents may play a unique role in accessing membrane proteins (Norris, et al., *Analytical Chemistry* 2003, 75, 6642-6647). Testing of many of these detergents and detergent application techniques that should enhance tryptic digestion and materially improve peptide conspicuity and protein identification are under way. These techniques should be applicable to MALDI and are the subject of continuing investigations in our laboratory.

DT-MALDI has shown itself to be semi-quantitative and sufficiently sensitive to register differences in the amount of protein present in situ, as indicated in FIG. 3. There was a progressive fall in the 65 kDa protein intensity with increasing distance from the brain lesion. An increase in the quantitative capabilities of the methods described here should be achievable with the application of a combination of synthetic matrices, detergents, solvents, and proteases.

Because this is a feasibility study, we followed certain goals in making our identifications. As expected, the proteins identified in these studies are normal constituents of these cells and tissues. Therefore, we did not perform additional studies, such as Western analysis, to further confirm their identities or attempt to obtain precise quantitative data to match our results. However there were large numbers of mass charge peaks in these specimens, indicating the presence of many known, and some unidentified proteins Moreover, visualized mass charge spectral peaks only represent the most abundant proteins. In addition, absent protein signatures merely implies no signal, not absent proteins. The sensitivity, precision, accuracy, and specificity of DT-MALDI are notable. It is theoretically possible for MALDI TOF with tandem mass spectrometers to register attomole quantities of proteins or peptides similar to MALDI analysis of gels without extraction or homogenation of tissue (Friedman, et al., *Proteomics* 2004, 4, 793-811; Fujii Kazuyasu, et al., *Proteomics* 2005, 5, 4274-4286; Hachey, et al., *Journal of Reproductive Immunology* 2004, 63, 61-73; O'Connor, et al., *Rapid Communications in Mass Spectrometry* 2006, 20, 259-266; Escobar, et al., *Journal of Pediatric Surgery* 2005, 40, 349-35829, 30, 31-33). Through the use of micro techniques tissue preparation and robotics it was possible to delineate the progress of a lesion across small distances in the brain. With the perfection of these and emerging micro-laser techniques, there may be a possibility of direct, in situ, intracellular identification of changes in the protein makeup of single cells.

The importance of the methods used for data mining and their application are critical. All values inserted into the Mascot© software syntax were manually verified from the m/z spectra. In this initial study it was believed that manual verification was essential. In future work, automation will ease this time consuming verification.

Precise and reproducible sample preparation which includes robotic control choice of detergents, protease digestants, and matrices are essential components of accurate protein determination. This will be especially important in the identification of low level protein species, one of the specific aims of our continuing studies.

The studies performed here demonstrate the ability of DT-MALDI to furnish rapid, direct identification of proteins in situ in cells and tissue without protein extraction. DT-MALDI appears to be a good tool for identification and relative quantification of specific proteins and peptides. The relative ease and speed of tissue preparation should allow early migration of DT-MALDI from the laboratory to clinical practice where it can become the basis for identification of protein and non-protein biological molecules characteristic of clinical disease.

The Mascot search results are depicted in FIGS. 5-18, as shown below. The use of Mascot for such analysis is described in the following references. (Electrophoresis 1999; 20(18):3551-3567, Probability-based protein identification by searching sequence databases using mass spectrometry data, Perkins, et al., *Electrophoresis,* 19(6) 893-900 (1998); Bleasby, et al., *Protein Eng.,* 3(3) 153-9 (1990). Peptide Mass Fingerprint; Pappin, et al., *Curr. Biol.,* 3(6) 327-32 (1993); James, et al., *Protein Sci,* 3(8) 1347-50 (1994). Sequence Query; Mann, et al., M and Wilm, M, Error-tolerant identification of peptides in sequence databases by peptide sequence tags. Anal Chem, 66(24) 4390-9 (1994); Pappin, et al. *Mass Spectrom. Biol. Sci.,* 135-50 (1996), MS/MS Ions Search; Eng, et al., *J. Am. Soc. Mass Spectrom.,* 5(11) 976-89 (1994)).

FIGS. 5-10. Histone H2B detailed Mascot search. Note Mascot score and search parameters.

Figure 12:
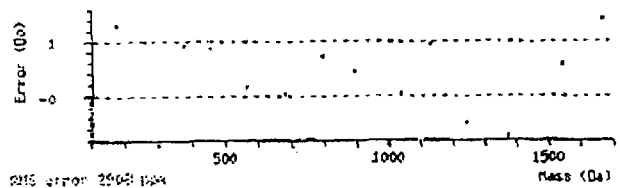
FIG. 12 provides the results of a histone H2B Mascot peptide analysis.

FIGS. 11-12 Histone H2B Mascot peptide analysis. Note large number of concordant matches in the y series.

FIGS. 13-18 Stroke model tubulin detailed Mascot search. Note Mascot score and search parameters.

What is claimed is:

1. A method for analyzing the biological molecule content of a tissue sample in situ, comprising:
   a. collecting a sample of tissue from a subject into a first solution capable of maintaining integrity of the biological molecule;
   b. treating the sample with a second solution comprising one or more enzymes, or chemicals, capable of dissociating the tissue sample or of digesting the dissociated tissue sample into smaller fragments;
   c. treating the preparation from step b) with a matrix assisted laser desorption ionization imaging (MALDI) matrix solution; and
   d. analyzing the preparation from step c) by direct tissue (DT)-matrix assisted laser desorption ionization imaging (MALDI)-time of flight (TOF) measurement or DT-MALDI-TOF-TOF measurement;
   e. creating a data file utilizing the information from step d);
   f. entering the data from the data file of step e) into an external database to create a signature map for the tissue from which the data was obtained; and
   g. comparing the results from step d) with a signature map for normal tissue, wherein said normal tissue corresponds to, or is of the same tissue type, as the tissue from which the sample was obtained.

2. The method of claim 1, wherein the method provides for both qualitative identification of the biological molecules in the sample, as well as, a quantitative measurement of the proteins biological molecules in the sample.

3. The method of claim 1, wherein the method provides for a level of detection of the biological molecules in the sample in an amount ranging from about 1 attamol to about 10 attamols.

4. The method of claim 1, wherein the collection device is a microcapillary pipette, a plastic or glass tube, or a slide for a cellular or tissue sample obtained from a microtime or an ultra cryo microtome.

5. The method of claim 1, wherein the first solution is a buffered solution or an alcohol.

6. The method of claim 5, wherein the buffered solution is selected from the group consisting of phosphate buffered saline (PBS), a phosphate buffer, a potassium buffer, a choline buffer and a glycine buffer.

7. The method of claim 5, wherein the alcohol is selected from the group consisting of methanol, ethanol, propanol, butanol, isopropyl alcohol and isobutanol.

8. The method of claim 1, wherein the one or more enzymes capable of dissociating the tissue and degrading the tissue into peptide fragments are selected from the group consisting of a collagenase, a lipase and a protease.

9. The method of claim 8, wherein the one or more enzymes are left in contact for a time and at a temperature sufficient to obtain dissociated tissue and peptide fragments.

10. The method of claim 9, wherein the time ranges from about 10 minutes to about 24 hours.

11. The method of claim 9, wherein the temperature ranges from about 20° C. to about 60° C.

12. The method of claim 1, wherein the MALDI matrix is selected from the group consisting of $\alpha$-4 cyano hydroxycinnamic acid (CHCA), sinnapinic acid, p-nitroaniline, a heavy metal and glycerol.

13. The method of claim 1, wherein the tissue sample is obtained from normal tissue, or abnormal/diseased tissue.

14. The method of claim 13, wherein the diseased tissue is a tumor tissue, tissue from a hyperproliferative disorder other than cancer, or an ischemic tissue.

15. The method of claim 14, wherein the hyperproliferative disorder other than cancer is selected from the group consisting of rheumatoid arthritis, lupus, multiple sclerosis, psoriasis and other autoimmune diseases.

16. The method of claim 14, wherein the tumor tissue is obtained from a benign tumor or a malignant tumor.

17. The method of claim 14, wherein the ischemic tissue is obtained from the brain, spinal cord or other nervous system tissue.

18. The method of claim 14, wherein the ischemic tissue is obtained from the heart or intestinal tract.

19. The method of claim 13, wherein the normal or abnormal/diseased tissue is selected from the group consisting of solid tissue or non-solid tissue.

20. The method of claim 19, wherein the solid tissue is selected from the group consisting of nervous system tissue, cardiac tissue, breast tissue, lung tissue, bladder tissue, gastrointestinal tissue, eyes, bone and tissue from any solid tumor.

21. The method of claim 19, wherein the non-solid tissue is selected from the group consisting of whole blood or isolated blood cells.

22. The method of claim 21, wherein the isolated blood cells are red blood cells or white blood cells.

23. The method of claim 22, wherein the white blood cells are selected from the group consisting of lymphocytes, polymorphonuclear cells (PMNs), monocytes and macrophages.

24. A method for identifying the presence of abnormal or diseased tissue in a subject comprising:
   a. collecting at least two different tissue samples, one of which is obtained from an area suspected of being diseased or abnormal and the second being normal tissue of the same tissue type;
   b. treating the tissue samples with a solution of one or more enzymes, or chemicals, capable of digesting the tissue samples into smaller fragments;
   c. treating the preparation from step b) with a MALDI matrix solution; and d. analyzing the preparation from step c) by DT-MALDI-TOF measurement or DT-MALDI-TOF-TOF measurement, wherein the analyzing comprises comparing the biological molecule content of the at least two different tissue samples, and wherein the biological molecule content of the at least two different tissue samples is compared to a signature map for normal tissue or abnormal or diseased tissue of the same tissue type.

25. The method of claim 24, wherein the signature map of the normal or diseased tissue is obtained from a pre-determined standard or from a known database of proteins isolated and characterized for that tissue and the specific disease of which the subject is suspected of having or at risk for developing.

26. A method for identifying the extent of tumor cell extravasation comprising:
   a) collecting two or more contiguous tissue samples from a tumor mass and the surrounding tissue;
   b) treating the tissue samples with a solution of one or more enzymes, or chemicals, capable of digesting the tissue samples into smaller fragments;
   c) treating the preparation from step b) with a MALDI matrix solution; and
   d) analyzing the preparation from step c) by DT-MALDI-TOF measurement or DT-MALDI-TOF-TOF measurement, wherein the analyzing comprises comparing the biological molecule content of the two or more contiguous tissue samples, wherein the biological molecule content of the two or more contiguous tissue samples is compared to a signature map for normal tissue or abnormal or diseased tissue of the same tissue type.

27. A method for analyzing the protein content of a cell or bodily fluid sample in situ, comprising:
   a) collecting a sample of tissue from a subject into a collection device containing a first solution capable of maintaining biological molecule integrity;
   b) treating the sample with a second solution comprising one or more enzymes, or chemicals, capable of digesting the tissue sample into smaller fragments;
   c) treating the preparation from step b) with a matrix assisted laser desorption ionization imaging (MALDI) matrix solution; and
   d) analyzing the preparation from step c) by direct tissue (DT)-matrix assisted laser desorption ionization imaging (MALDI)-time of flight (TOF) measurement or DT-MALDI-TOF-TOF measurement;
   e) creating a data file utilizing the information from step d);
   f) entering the data from the data file of step e) into an external database to create a signature map for the tissue from which the data was obtained; and
   comparing the results from step d) with a signature map for normal tissue, wherein said normal tissue corresponds to the tissue from which the sample was obtained.

28. The method of claim 27, wherein the cell or bodily fluid is selected from the group consisting of urine, serum, plasma, cerebrospinal fluid (CSF), sputum, bone marrow, amniotic fluid and bronchial lavage.

29. A method for determining the presence of a disease in a subject, or for assessing a subject's risk for developing said disease, or for determining a subject's response to a particular therapy for said disease, or for distinguishing between a responder or a non-responder for a particular therapy, the method comprising:
   a. collecting a first tissue sample from a subject suspected of having a disease or being at risk for developing a disease or being treated for a disease;
   b. collecting a second cellular or bodily fluid sample from the same subject;
   c. treating the first tissue sample with a solution comprising one or more enzymes, or chemicals, capable of digesting the first tissue sample into fragments and treating the second cellular or bodily fluid sample with a solution comprising one or more enzymes, or chemicals capable of digesting the second cellular or bodily fluid sample into fragments;
   d. treating the first tissue sample and the second cellular or bodily fluid sample preparations from step c) with a matrix assisted laser desorption ionization imaging (MALDI) matrix solution; and
   e. analyzing the preparations from step c) by direct tissue (DT)-matrix assisted laser desorption ionization imaging (MALDI)-time of flight (TOF) measurement or DT-MALDI-TOF-TOF measurement;
   f. comparing the results from step e) with a signature map for normal tissue, wherein said normal tissue corresponds to the tissue from which the first tissue sample was obtained, and a signature map for normal cells or bodily fluid, wherein the normal cells or bodily fluid correspond to the cells or bodily fluid sample obtained from the subject suspected of having or being at risk for developing said disease, or being treated for said disease.

30. A method for determining the disposition of a new chemical entity or new biological entity in a cell or tissue in vivo, comprising:
   a) collecting a sample of a tissue or cell from a subject into a first solution capable of maintaining integrity of the tissue or cell sample, prior to treating the subject with a new chemical entity or new biological entity;
   b) administering a new chemical entity or new biological entity to said subject;
   c) collecting a series of tissue or cell samples from the subject into a first solution capable of maintaining integrity of the tissue or cell sample at various time points after administering the new chemical entity or new biological entity;
   d) treating the samples with a second solution comprising one or more enzymes, or chemicals, capable of dissociating the tissue sample or of digesting the dissociated tissue sample into smaller fragments;
   e) treating the preparation from step d) with a matrix assisted laser desorption ionization imaging (MALDI) matrix solution; and
   f) analyzing the preparation from step e) by direct tissue (DT)-matrix assisted laser desorption ionization imaging (MALDI)-time of flight (TOF) measurement or DT-MALDI-TOF-TOF measurement; and
   g) comparing the results from step f) with a series of tissue or cell samples, comparable to the tissue or cell samples collected from the subject, to which has been added either the new chemical entity or new biological entity;
   h) obtaining a signature map or profile for the new chemical or new biological entity in the series of tissue or cell samples for monitoring the presence or absence of the new chemical entity or new biological entity in the same type of tissue or cell sample from the patient, and
   i) determining the presence and/or amount of the new chemical entity or new biological entity in said tissue or cell samples.

31. A method for determining the disposition of a new chemical entity or new biological entity in a cell or tissue in situ, comprising:
  a) collecting a sample of a tissue or cell from a first subject into a first solution capable of maintaining integrity of the tissue or cell sample, prior to treating the first subject with a new chemical entity or new biological entity;
  b) administering a new chemical entity or new biological entity to said first subject;
  c) collecting a series of tissue or cell samples from the first subject into a first solution capable of maintaining integrity of the tissue or cell sample at various time points after administering the new chemical entity or new biological entity;
  d) treating the samples with a second solution comprising one or more enzymes, or chemicals, capable of digesting the tissue sample into smaller fragments;
  e) treating the preparation from step d) with a matrix assisted laser desorption ionization imaging (MALDI) matrix solution; and
  f) analyzing the preparation from step e) by direct tissue (DT)-matrix assisted laser desorption ionization imaging (MALDI)-time of flight (TOF) measurement or DT-MALDI-TOF-TOF measurement; and
  g) comparing the results from step f) with a series of tissue or cell samples collected from a second subject, wherein said second subject has not been administered the new chemical entity or new biological entity, wherein the tissue or cell samples collected from the second subject are identical or comparable to the tissue or cell sample collected from the first subject;
  h) obtaining a signature map or profile for the new chemical or new biological entity in the series of tissue or cell samples for monitoring the presence or absence of the new chemical entity or new biological entity in the same type of tissue or cell sample from any other subject to be treated in the future with the new chemical entity or new biological entity.

32. A method for determining the intracellular location of a new chemical entity or new biological entity comprising:
  a) collecting a cell sample, prior to treating the sample with a new chemical entity or new biological entity, into a solution capable of maintaining cellular integrity;
  b) treating said cell sample with a new chemical entity or new biological entity;
  c) treating the cell sample from step a) or b) with a second solution comprising one or more enzymes, or chemicals, capable of digesting the cell samples into smaller fragments;
  d) treating the samples from step c) with a matrix assisted laser desorption ionization imaging (MALDI) matrix solution; and
  e) analyzing the preparation from step d) by direct tissue (DT)-matrix assisted laser desorption ionization imaging (MALDI)-time of flight (TOF) measurement or DT-MALDI-TOF-TOF measurement; and
  f) comparing the results from step b) with the results from step a) to determine the presence of the new chemical entity or new biological entity in the cell sample from step b).

* * * * *